United States Patent
Rahn et al.

(10) Patent No.: US 7,260,253 B2
(45) Date of Patent: Aug. 21, 2007

(54) METHOD FOR CORRECTION OF RELATIVE OBJECT-DETECTOR MOTION BETWEEN SUCCESSIVE VIEWS

(75) Inventors: John Richard Rahn, Sammamish, WA (US); Alan C. Nelson, Gig Harbor, WA (US)

(73) Assignee: VisionGate, Inc., Gig Harbor, WA (US)

( * ) Notice: Subject to any disclaimer, the term of this patent is extended or adjusted under 35 U.S.C. 154(b) by 215 days.

(21) Appl. No.: 10/876,328

(22) Filed: Jun. 24, 2004

(65) Prior Publication Data

US 2005/0010108 A1 Jan. 13, 2005

Related U.S. Application Data

(63) Continuation-in-part of application No. 10/126,026, filed on Apr. 19, 2002.

(51) Int. Cl.
*G06K 9/00* (2006.01)
*G21K 1/12* (2006.01)

(52) U.S. Cl. .......................... 382/131; 382/295; 378/21

(58) Field of Classification Search ................ None
See application file for complete search history.

(56) References Cited

U.S. PATENT DOCUMENTS

| | | | |
|---|---|---|---|
| 3,470,373 A | 9/1969 | Brewer | |
| 3,497,690 A | 2/1970 | Wheeless, Jr. | |
| 3,598,471 A | 8/1971 | Baldwin | |
| 3,657,537 A | 4/1972 | Wheeless, Jr. | |
| 3,748,468 A | 7/1973 | Hartman | |
| 3,833,762 A | 9/1974 | Gudmundsen | |
| 3,960,449 A | 6/1976 | Carlton | |
| 3,999,047 A | 12/1976 | Green | |
| 4,175,860 A | 11/1979 | Bacus | |
| 4,183,623 A | 1/1980 | Haines | |
| 4,200,353 A | 4/1980 | Hoffman | |
| 4,293,221 A | 10/1981 | Kay | |
| 4,360,885 A | 11/1982 | Edgar | |
| 4,714,345 A | 12/1987 | Schrader | |
| 4,858,128 A | 8/1989 | Nowak | |
| 4,873,653 A | 10/1989 | Grosskopf | |
| 4,891,829 A | 1/1990 | Deckman | |
| 5,141,609 A | 8/1992 | Sweedler et al. | |

(Continued)

FOREIGN PATENT DOCUMENTS

WO   WO 02/095476 A2   11/2002

OTHER PUBLICATIONS

Kikuchi, S. et al., "Three-dimensional computed tomography for optical microscopes," Optics Communications 107 (1994) 432-444.

(Continued)

*Primary Examiner*—Matthew C. Bella
*Assistant Examiner*—Charles Kim
(74) *Attorney, Agent, or Firm*—George A. Leone

(57) ABSTRACT

Motion correction for optical tomographic imaging in three dimensions. An object of interest is illuminated to produce an image. A lateral offset correction value is determined for the image. An axial offset correction value is determined for the image. The lateral offset correction value and the axial offset correction value are applied to the image to produce a corrected file image.

15 Claims, 10 Drawing Sheets

U.S. PATENT DOCUMENTS

| | | | |
|---|---|---|---|
| 5,148,502 | A | 9/1992 | Tsujiuchi et al. |
| 5,189,518 | A * | 2/1993 | Nishida ................ 348/208.11 |
| 5,281,517 | A | 1/1994 | Bacus et al. |
| 5,308,990 | A | 5/1994 | Takahashi et al. |
| 5,312,535 | A | 5/1994 | Waska et al. |
| 5,321,501 | A | 6/1994 | Swanson et al. |
| 5,402,460 | A | 3/1995 | Johnson |
| 5,552,605 | A * | 9/1996 | Arata .................... 250/363.04 |
| 5,668,887 | A | 9/1997 | Parker et al. |
| 5,673,300 | A * | 9/1997 | Reckwerdt et al. ........... 378/65 |
| 5,680,484 | A | 10/1997 | Ohyama et al. |
| 5,710,429 | A | 1/1998 | Alfano et al. |
| 5,741,411 | A | 4/1998 | Yeung et al. |
| 5,757,981 | A * | 5/1998 | Kawakubo .................. 382/293 |
| 5,760,901 | A | 6/1998 | Hill |
| 5,760,951 | A | 6/1998 | Dixon et al. |
| 5,828,408 | A | 10/1998 | Mottin et al. |
| 5,848,123 | A | 12/1998 | Strommer |
| 5,878,103 | A | 3/1999 | Sauer et al. |
| 5,880,838 | A | 3/1999 | Marx et al. |
| 5,909,476 | A | 6/1999 | Cheng et al. |
| 5,915,048 | A | 6/1999 | Hill et al. |
| 5,987,158 | A | 11/1999 | Meyer |
| 6,005,617 | A | 12/1999 | Shimamoto et al. |
| 6,026,174 | A | 2/2000 | Palcic |
| 6,038,067 | A | 3/2000 | George |
| 6,047,080 | A | 4/2000 | Chen et al. |
| 6,072,624 | A | 6/2000 | Dixon et al. |
| 6,091,983 | A | 7/2000 | Alfano et al. |
| 6,130,958 | A | 10/2000 | Rohler et al. |
| 6,165,734 | A | 12/2000 | Garini |
| 6,192,144 | B1 * | 2/2001 | Holz .......................... 382/131 |
| 6,201,628 | B1 | 3/2001 | Basiji |
| 6,211,955 | B1 | 4/2001 | Basiji |
| 6,215,587 | B1 | 4/2001 | Alfano et al. |
| 6,239,871 | B1 | 5/2001 | Gilby |
| 6,248,988 | B1 | 6/2001 | Krantz |
| 6,249,341 | B1 | 6/2001 | Basiji |
| 6,251,586 | B1 | 6/2001 | Mulshine |
| 6,251,615 | B1 | 6/2001 | Oberhardt |
| 6,252,979 | B1 | 6/2001 | Lee |
| 6,312,914 | B1 | 11/2001 | Kardos et al. |
| 6,388,809 | B1 | 5/2002 | MacAulay |
| 6,452,179 | B1 | 9/2002 | Coates et al. |
| 6,519,355 | B2 | 2/2003 | Nelson |
| 6,522,775 | B2 | 2/2003 | Nelson |
| 6,529,614 | B1 | 3/2003 | Chao et al. |
| 6,591,003 | B2 | 7/2003 | Chu |
| 6,636,623 | B2 | 10/2003 | Nelson |
| 6,640,014 | B1 | 10/2003 | Price et al. |
| 6,697,508 | B2 | 2/2004 | Nelson |
| 6,741,730 | B2 | 5/2004 | Rahn |
| 6,775,399 | B1 * | 8/2004 | Jiang .......................... 382/128 |
| 6,868,177 | B1 * | 3/2005 | Camahort et al. .......... 382/154 |
| 2001/0012069 | A1 | 8/2001 | Derudinger et al. |
| 2002/0161534 | A1 | 10/2002 | Adler et al. |
| 2003/0210760 | A1 | 11/2003 | Nelson |
| 2003/0222197 | A1 | 12/2003 | Reese |
| 2004/0001618 | A1 | 1/2004 | Johnson |
| 2004/0008515 | A1 | 1/2004 | Brown |
| 2004/0076319 | A1 | 4/2004 | Fauver |
| 2005/0006595 | A1 | 1/2005 | Goodwin et al. |

OTHER PUBLICATIONS

Kikuchi, S. et al., "Three-dimensional microscopic computed tomography based on general Radon transform for optical imaging systems," Optics Communications 123 (1996).

Matula, P. et al. "Precise 3D image alignment in micro-axial tomography," Journal of Microscopy, vol. 209, Pt. 2 (Feb. 2003) pp. 126-142.

Ong, SH, Development of an imaging flow cytometer. Anal Quant Cytol Histol 9(5)pp. 375-382, 1987.

Gilbert, P, "Iterative Methods for the Three dimensional Reconstruction of an Object from Projections," Journal of Theoretical Biology 36pp. 105-117, 1972.

Oppenheim, BE, More Accurate Algorithms for Iterative 3 dimensional Reconstruction, IEEE Transactions on Nuclear Science NS-21pp. 72-77, 1974.

Singer, JR, Grunbaum, FA, Kohn, P, and Zubelli, JP, "Image Reconstruction of the Interior of Bodies that Diffuse Radiation," Science 248(4958)pp. 990-993, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12)pp. 1227-1237, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32pp. 205-216, 1971.

Manglos, SH, Jaszcak, RJ, and Floyd, CE, "Maximum Likelihood Reconstruction for Cone Beam SPECT: Development and Initial Tests," Physics in Medicine and Biology 34(12)pp. 1947-1957,1989, #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7)pp. 1225-1241, 1995, #4389.

Hampel, U and Freyer, R, "Fast Image Reconstruction for Optical Absorption Tomography in Media with Radially Symmetric Boundaries", Medical Physics 25 (1)pp. 92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2)pp. 183-193, 1998.

Herman, G, Image Reconstruction from Projections: The Fundamentals of Computerized Tomography, Academic Press, New York, 1980.

Paulsen, KD and Jiang, H, "Spatially Varying Optical Property Reconstruction Using a Finite Element Diffusion Equation Approximation", Medical Physics 22(691-701) 1995.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, Pratical Flow Cytometry, 3rd ed., Wiley-Liss, 1995.

HJ Tiziani and MI Uhde, Three-dimensional analysis by a microlens array confocal arrangements (Applied Optics 33, 567 [1994]).

Bayat, S, Le Duc, G, Porra, L, Berrruyer, G, Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney, JH and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," SCIENCE, vol. 296, pp. 541-545, Apr. 19, 2002.

Sharpe, J, review, "Optical Projection Tomography as a New Tool for Studying Embryo Anatomy," *J. Anat.* (2003), pp. 175-181.

RH Anderson, "Close-up imaging of documents and displays with lens arrays," *Applied Optics* 18, 477 (1979).

Kak, A.C. and Slaney, M., *Principles of Computerized Tomographic Imaging*, IEEE Press, New York, 1988.

E.G. Steward, *Fourier Optics: An Introduction*, 2nd ed. (Halsted Press, New York, 1987).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements, " Cytometry, vol. 2, No. 5, pp. 327-336 (1982).

M. Rozycka, et al., "Optical Diffraction as a Tool for Semiautomatic , Quantitative Analysis of Tissue Specimens," Cytometry, vol. 2, No. 4, pp. 244-248 (1982).

Almeida and Fuji, Fourier transform differences and averaged similarities in diatoms, Applied Optics, vol. 18, No. 10, pp. 1663-1667, (1979).

Smolinska and Dawidowicz, "Extraction of common or different part from optical images," Institute of Physics, Warsaw Technical University, 222-223.

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149-156, 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78:435-449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504-509.

George, JS et al., "Virtual Pinhole Confocal Microscope," Physics Division Progress Report, www.lanl.gov/p/pdfs/papp_pinhole.pdf, (1999-2000).

Pawley, JB, *Handbook of Biological Confocal Microscopy*, Plenum Press, NY, 479-490 (1995).

Reymond and Pickett-Heaps (1983), entitled "A Routine Flat Embedding Method for Electron Microscopy of Microorganisms Allowing Selection and Precisely Orientated Sectioning of Single Cells by Light Microscopy," Journal of Microscopy, vol. 130, Pt. 1, Apr. 1983, pp. 79-84.

Nicewarner-Peña et al., "Submicrometer Metallic Barcodes," *Science* 294, 137 (2001).

Schmitz et al., "Performance Characteristics of a Silicon Photodiode (SiPD) Based Instrument for Fast Functional Optical Tomography," SUNY Downstate Medicial Center, Brooklyn, NY 11203.

Schmitz et al., "Instrument for Real-Time Dynamic Optical Tomography," SUNY Downstate Medicial Center, Brooklyn, NY 11203.

Polymicro Technologies "Square Flexible Fused Silica Capillary Tubing," (2003) www.polymicro.com.

Shannon, *The Art and Science of Optical Design*, (1977) University of Arizona, Cambridge University Press, Fig. 4.12 and Fig. 4.13.

\* cited by examiner

METHOD FOR CORRECTION OF RELATIVE OBJECT-DETECTOR MOTION BETWEEN SUCCESSIVE VIEWS

RELATED APPLICATIONS

This application is a continuation-in-part (CIP) of co-pending U.S. patent application Ser. No. 10/126,026, filed Apr. 19, 2002, of Nelson, entitled "Variable Motion Optical Tomography of Small Objects," which is incorporated herein by this reference.

FIELD OF THE INVENTION

The present invention relates to imaging and, more particularly, to detection of and correction for relative object-detector motion in an imaging system where, typically, successive views from different positions are acquired, each view representing a two-dimensional projection or pseudo-projection of the three-dimensional object.

BACKGROUND OF THE INVENTION

An optical projection tomographic microscopy (OPTM) is suitable for high-resolution imaging of a microscopic object, such as a biological cell and its nucleus, which are embedded in a fluid medium and contained within a microcapillary tube having inner and outer diameters of 40 microns and 150 microns, respectively. An OPTM employs a plurality of views, each acquired by rotating the object and its containment vessel about an axis perpendicular to the optical axis and parallel to the axis of the microcapillary tube. A camera, having a CCD image sensor composed of an M×N array of pixels, captures the light after it has passed through the object and the imaging optics, which produce a magnified image of the field of view (FOV) on the CCD. Since each view is taken from a different perspective, the content of each view will differ from the others.

Owing to the extremely small sizes of the components, it can be quite difficult to position the axis of rotation (typically coincident with the central axis of the microcapillary tube) in the center of the detector's FOV. It is further very difficult to hold the microcapillary tube stationary while rotating it. In addition, the cell itself may move along the tube axis in between views. As a result, each view, which is already altered due to the tube rotation, can in addition be subject to translations both axial (parallel to the microcapillary axis) and lateral (perpendicular to the optical axis and to the tube axis). These lateral translations are in addition to those already present for objects that are not on the rotation axis.

In order to obtain an accurate 3D reconstruction, whether through filtered backprojection or other means, it is therefore necessary to correct for the axial motion and for that portion of the lateral motion that is not due to the changing perspective from one view to another. It is further necessary to determine where in the detector FOV the axis of rotation is located.

U.S. Pat. No. 4,858,128, to Nowak describes a method where consecutive scenes are correlated with one another, first in one axis and then, independently, in the other axis. The location of the maximum value for the two correlations determines the required offset for the two axes. The method described fails to provide means for distinguishing the "natural" lateral translation, due to the change in perspective, from the "erroneous" lateral translation, due to translation of the microcapillary tube. The Nowak patent teaches, "it may be useful to estimate such background component of the signal and to subtract the estimate from the image data."

William H. Press et al., *Numerical Recipes in C: The Art of Scientific Computing*, Cambridge University Press; 2nd edition (Jan. 1, 1993) describe means for implementing, via a computer program, the techniques of cross-correlation between two arrays of data using fast Fourier transforms (FFTs). In brief, the cross-correlation of two data arrays (such as image data) can be obtained by applying an FFT to each array, multiplying one of the resulting arrays by the complex conjugate of the other, and applying an inverse FFT to the result.

In order to overcome current shortcomings in the state of the art, it is an objective of the present invention to provide a method for finding the location of the central axis of a microcapillary tube for each view in a multi-view imaging system. It is a further objective of the invention to provide a method for detecting relative object-detector motion between successive views in a multi-view imaging system. It is a further objective of the invention to provide a method for correcting image data to remove errors due to object motion during image data collection. It is a still further objective of the invention to provide an imaging system of a type producing a plurality of X-Y data matrices representing projection or pseudo-projection views of an object for subsequent tomographic reconstruction of axial slices of the object. The detected motion may be removed by suitably shifting later data to align it with earlier data, or vice versa.

SUMMARY OF THE INVENTION

The present invention provides an apparatus and method for registration correction for optical tomographic imaging in three dimensions. An object of interest is illuminated to produce an image. A lateral offset correction value is determined for the image. An axial offset correction value is determined for the image. The lateral offset correction value and the axial offset correction value are applied to the image to produce a corrected file image.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings described hereinbelow.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited. Although the present invention may be employed in other types of imaging systems, such as, for example, X-ray computed tomography (CT) imaging, for concreteness of description the following disclosure is directed toward the invention in the environment of an optical projection tomographic microscopy (OPTM) system.

In the discussion that follows, the following assumptions are used when providing numerical examples:

1. Each image consists of an array, 640 pixels wide by 480 pixels high;

2. Each pixel contains a single 8-bit (gray level 0 to 255) brightness value;

3. With reference to an OPTM using a microcapillary tube, the tube axis is parallel to the shorter axis (480 pixels);

4. With reference to an OPTM using a microcapillary tube, the tube wall separation is 530 pixels;

5. The number of bins used in finding the lateral offset (B1) is 20;

6. The number of bins used in finding the axial offset (B2) is 2;

7. The array is zero-padded to 1024 by 1024 pixels.

It is to be understood that these numerical values are for illustrative purposes only; other numerical values may be employed without detracting from the nature of the invention.

Figure 1:
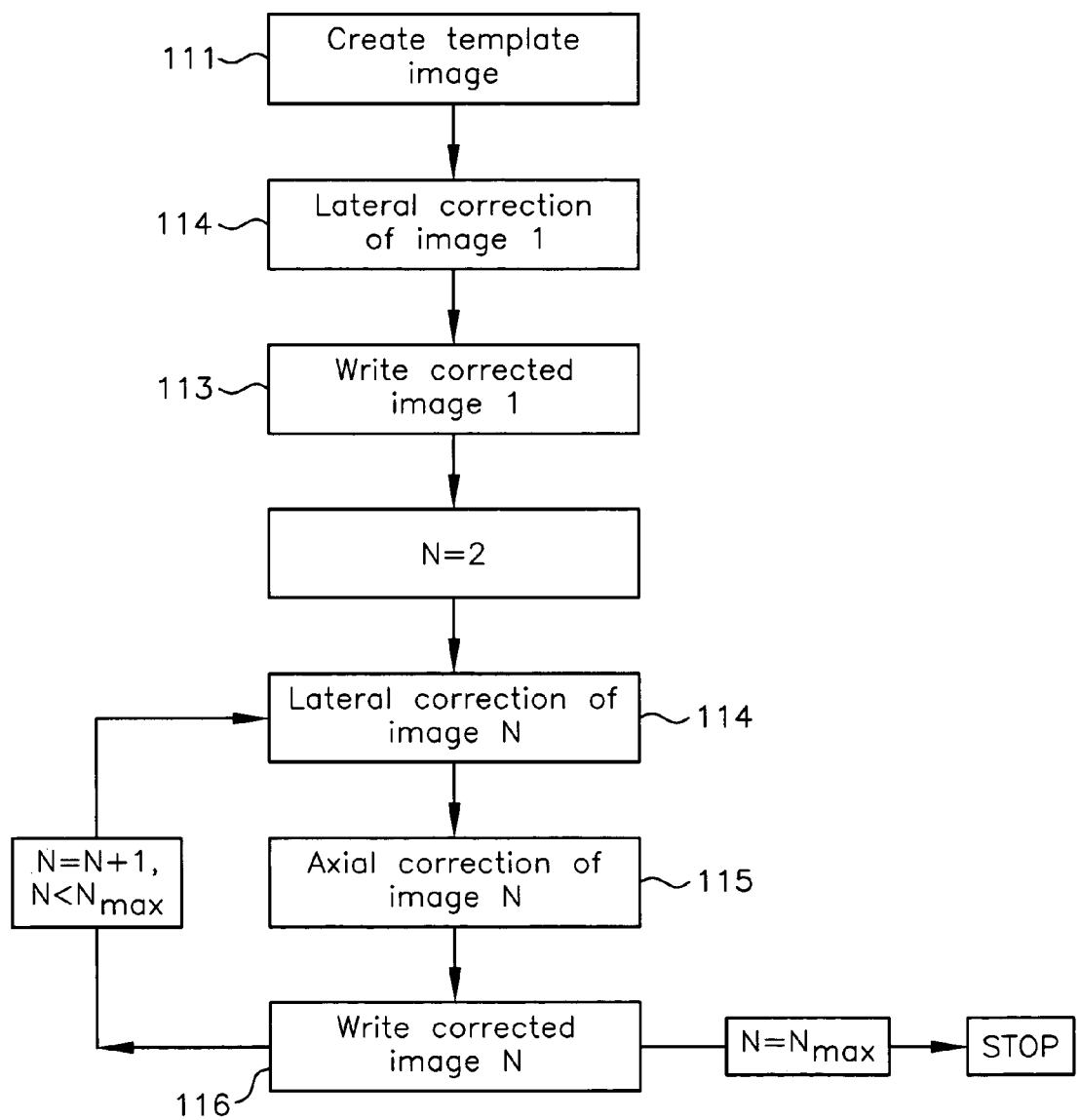
FIG. 1 is a functional block diagram of an example embodiment of a method for correction of relative object-detector motion between successive views constructed in accordance with the teachings of the present invention.

Referring now to FIG. 1, a functional block diagram of an example embodiment of a method for correction of relative object-detector motion between successive views constructed in accordance with the teachings of the present invention is shown. In the example embodiment, an altered copy of each image is generated, in which the brightest pixels are reassigned a brightness level of zero, while all other pixels retain the same brightness as in the initial image. A two-dimensional (2D) FFT of this thresholded image is then multiplied, pixel-by-pixel, with the complex conjugate of the 2D FFT of a reference image. The brightness of the resulting array is then summed along each line parallel to the axis of the microcapillary tube (to be referred to henceforth as the Y axis) to develop a one-dimensional (1D) array containing information about the brightness pattern in the direction (to be referred to henceforth as the X axis) perpendicular to the optical axis and to the microcapillary axis.

A 1D FFT is then applied, and the location of the maximum is determined. The location determines the amount of offset to be applied along the X axis in order to bring the image of the microcapillary tube's center axis to its desired position in the image.

The reference image takes advantage of the constancy of the separation between the walls of the microcapillary tube, and consists of two maximally bright lines separated by the known amount found in the acquired images; the rest of the reference image has zero brightness. The tube walls appear only faintly in the pseudo-projection images, as the refractive indices of the tube walls are matched with materials inside the tube and between the tube and the slide/coverslip assembly. The effect of the histogram operation is to enhance the contrast between the tube walls and the rest of the image. Using the pre-determined tube wall separation, in combination with the known number of pixels along the X axis of the image, makes it possible to distinguish the movement of the tube itself from the movement of the objects within the tube, due to the rotation of the tube and the consequent perspective change. By cross-correlating the two images based on a constant feature, our method minimizes the possibility of tracking the movements of changing features within the cell.

A cross-correlation method is used to determine the amount of the axial offset from the Y-axis. To do so, a copy of the original image is again thresholded, but using different criteria for determining which pixels are reset to zero brightness. A 2D FFT is applied to this image, and multiplied, pixel-by-pixel, with the complex conjugate of the 2D FFT of the thresholded image derived from the immediately preceding view. A 2D FFT is applied to the result, and the X-axis offset is determined as the maximum in the cross-correlation function along the line that corresponds to the difference in the lateral correction of the current image with that of the previous image. This is a distinction from previous methods, in that the X-axis is constrained by the Y-axis offset; it is not found independently of the Y-axis offset.

Unlike the lateral correction, the axial correction is an iterative process and thus is subject to cumulative errors. The axial cross-correlation functions effectively, however, as long as the change in perspective between consecutive images is not too large; this corresponds to small angular increments in the rotation. By keeping the angular increment small, the spatial content does not vary by much, allowing the cross-correlation to track similar features in each image. Since the angular increment also determines the lateral resolution of the 3D tomographic reconstruction, the requirement that the angular increment be kept small to allow the cross-correlation to work well is not an onerous one.

Briefly stated, this embodiment of the present invention removes the effects of axial and lateral movement by the microcapillary tube by suitably shifting subsequent images to align them with previous images, or vice versa. Cross-correlation methods are used to find the offset on the lateral axis, then on the tube axis, with the restriction that the peak correlation for the axial movement must come after the determination of the lateral movement.

The first step 111 is to generate the template image. Two white lines having, for example, a grayscale level of 65,535, are created at their ideal positions. Each line has a length of 480 pixels, running parallel to the short image dimension. The locations of the two lines are determined by the long image dimension (640 pixels) and the tube wall separation, empirically determined as 530 pixels. The first line is located at line 0 and the second line is located at line 530. In this embodiment, the size of the template image may be expanded from 640×480 to 1024×1024 to provide zero-padding in both dimensions; however, this action is not essential to the invention.

A 2D FFT is performed on the template image so that real and imaginary components are saved in alternating indices of the resulting array. Thus, for a zero-padded array, the array size is 2048×1024. The template image is now in a form ready for use.

At step 114 the lateral offset is found. In step 114, the image is thresholded in order to black out the background pixels, and then cross-correlated with the binary image of two bright lines. Images of interest are subject to the lateral offset determination 114. To assist in the axial correction, $D_{LAT}$ is saved for each image as indicated in step 29.

Figure 2:
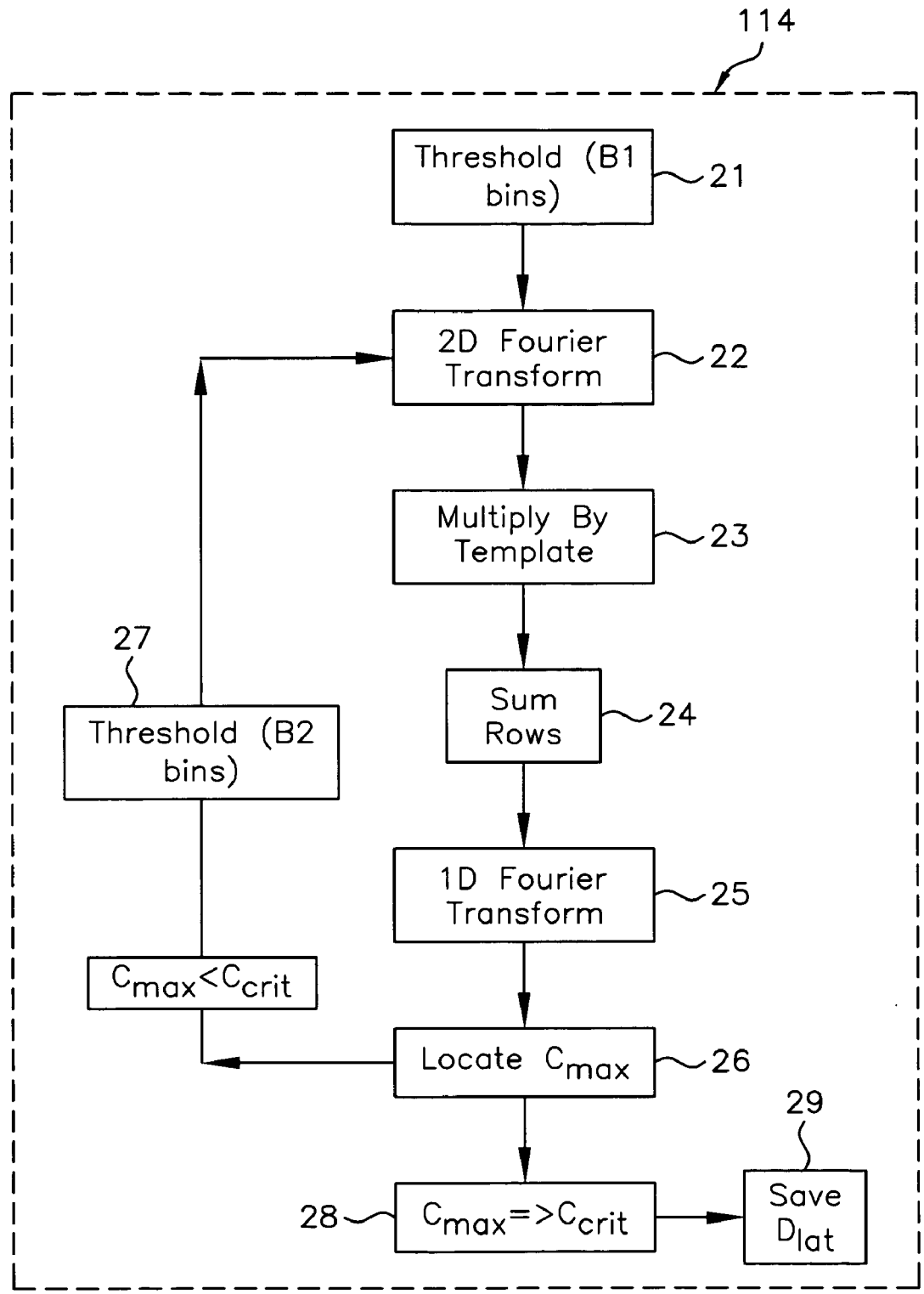
FIG. 2 is a functional block diagram of a lateral correction portion of an imaging system employing the example embodiment described in FIG. 1.

Referring now to FIG. 2, a functional block diagram of a lateral correction portion of an imaging system employing the example embodiment described in FIG. 1 is shown. The steps involved in finding the lateral offset 114 include constructing a grayscale histogram of the image, where the number of bins (B1) may be set at any integer value from 2 to 255. For the present example, it is assumed that B1=20. The bin with the greatest number of pixels is found (except the first bin, corresponding to the darkest pixels), and all pixels in the original image having that bin's grayscale value or higher are set equal to zero in a copy of the original image. The effect of this procedure 21 is to remove the background pixels from further consideration in order to produce a thresholded image.

As an example, suppose the input image has minimum and maximum grayscale values of 31 and 190, respectively, so that each bin has a width of eight gray levels [(1+190+31)/20=8]. Now further suppose that peak in the histogram occurs at bin #16 (i.e., gray levels from 151 to 158). Then the thresholded image will be similar to the original image, except that all pixels with an initial gray level greater than 150 now have a gray level of zero.

Figure 4B:
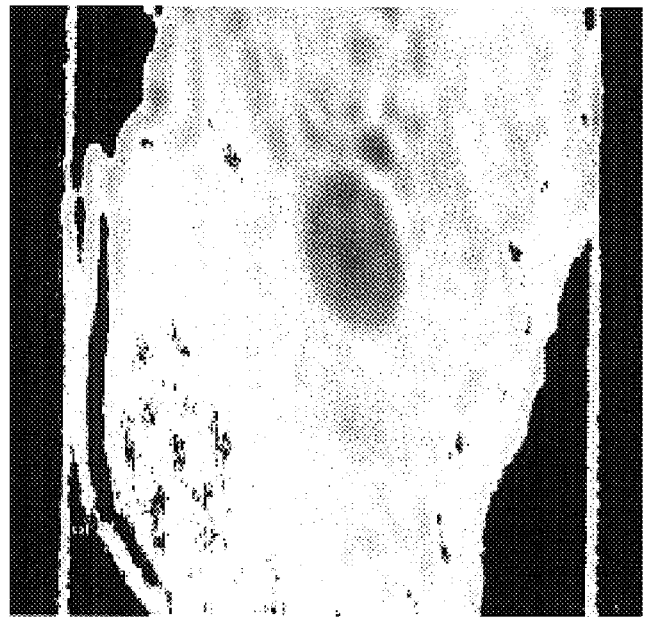
FIG. 4B depicts the result of applying thresholding operations that are employed in one example of the method of the present invention to the image shown in FIG. 4A.
Figure 4A:
FIG. 4A depicts an image of a cell prior to thresholding operations that are employed in one example of the method of the present invention.
Figure 4C:
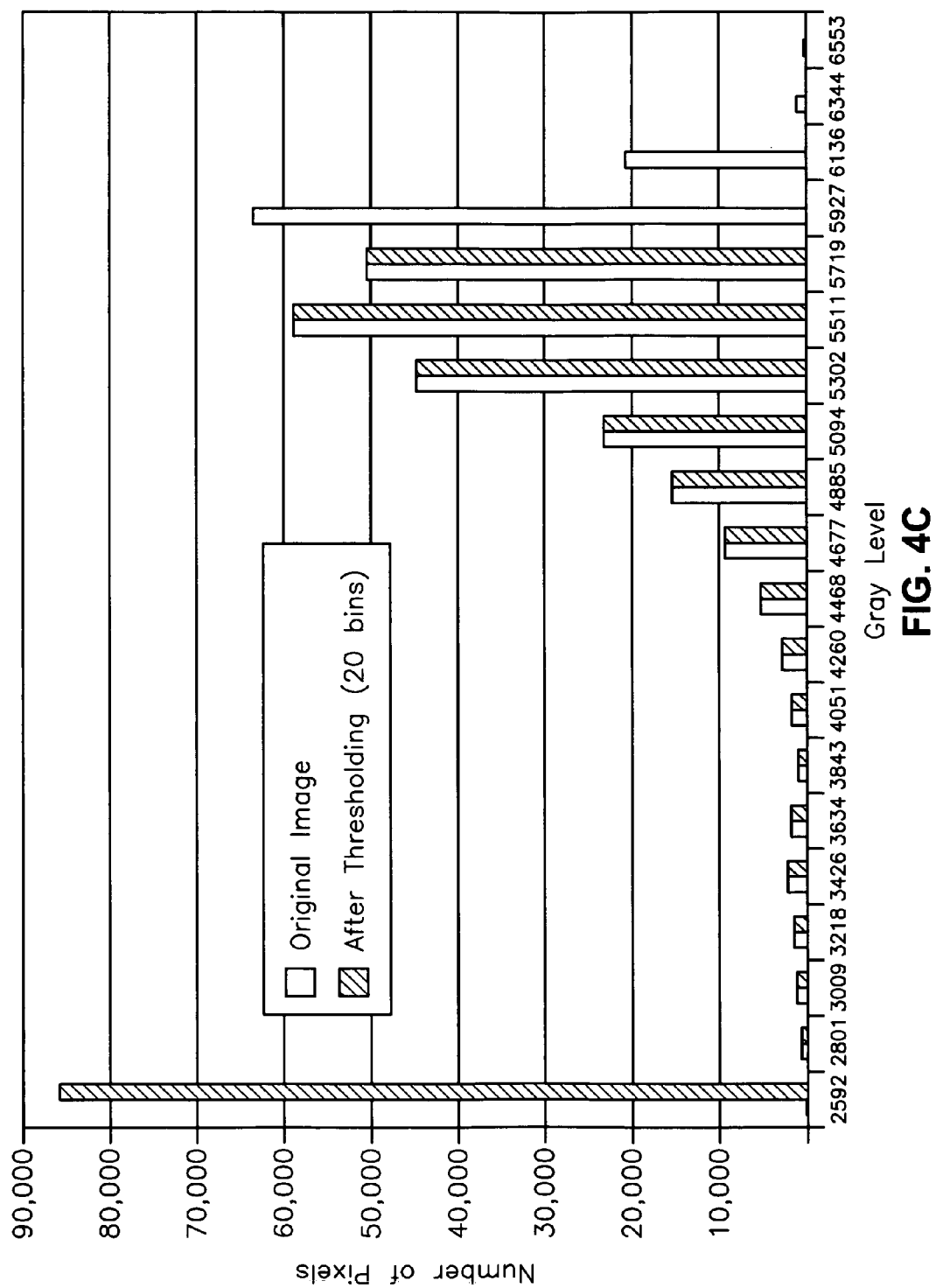
FIG. 4C illustrates a histogram showing brightness distributions of the images shown in FIGS. 4A–4B.

FIGS. 4A–4C illustrate the effect of applying these steps 21 to an image. A visual comparison of an original image to a segmented image may be made with reference to FIG. 4A, which shows an example of a cell image prior to segmentation and thresholding, and then to FIG. 4B which shows an example of a segmented and thresholded cell image corresponding to the original image of FIG. 4A. FIG. 4C is a histogram of an example image showing a comparison of the grey levels of the original image and the image after thresholding is applied.

A 2D FFT is applied to the thresholded image 22, and its Fourier transform is multiplied 23 by the complex conjugate of the Fourier transform of the template image. The resulting array is summed 24 along each of the 640 rows to compute a new array, which is Fourier transformed (in 1D) 25 to find the cross-correlation of the rows of the thresholded image and the reference image. The maximum value of the 1D array is located 26 and evaluated 28. The position of the maximum is designated as $D_{LAT}$ and its magnitude is designated as $C_{MAX}$.

The necessary offset is determined by the difference between $D_{LAT}$ and its ideal position of 55 [(640−530)/2=55]. Thus, for example, if $D_{LAT}$=63, then an upward shift of 8 pixels is necessary (63−55=8), while if $D_{LAT}$=41, then a downward shift of 14 pixels (55−14=14) is required.

The procedure 114 is repeated for all images in the data set. Note that each image is referenced to the same template, so there is no cumulative error. To assist in the axial correction, $D_{LAT}$ is saved 29 for each image.

Figure 3:
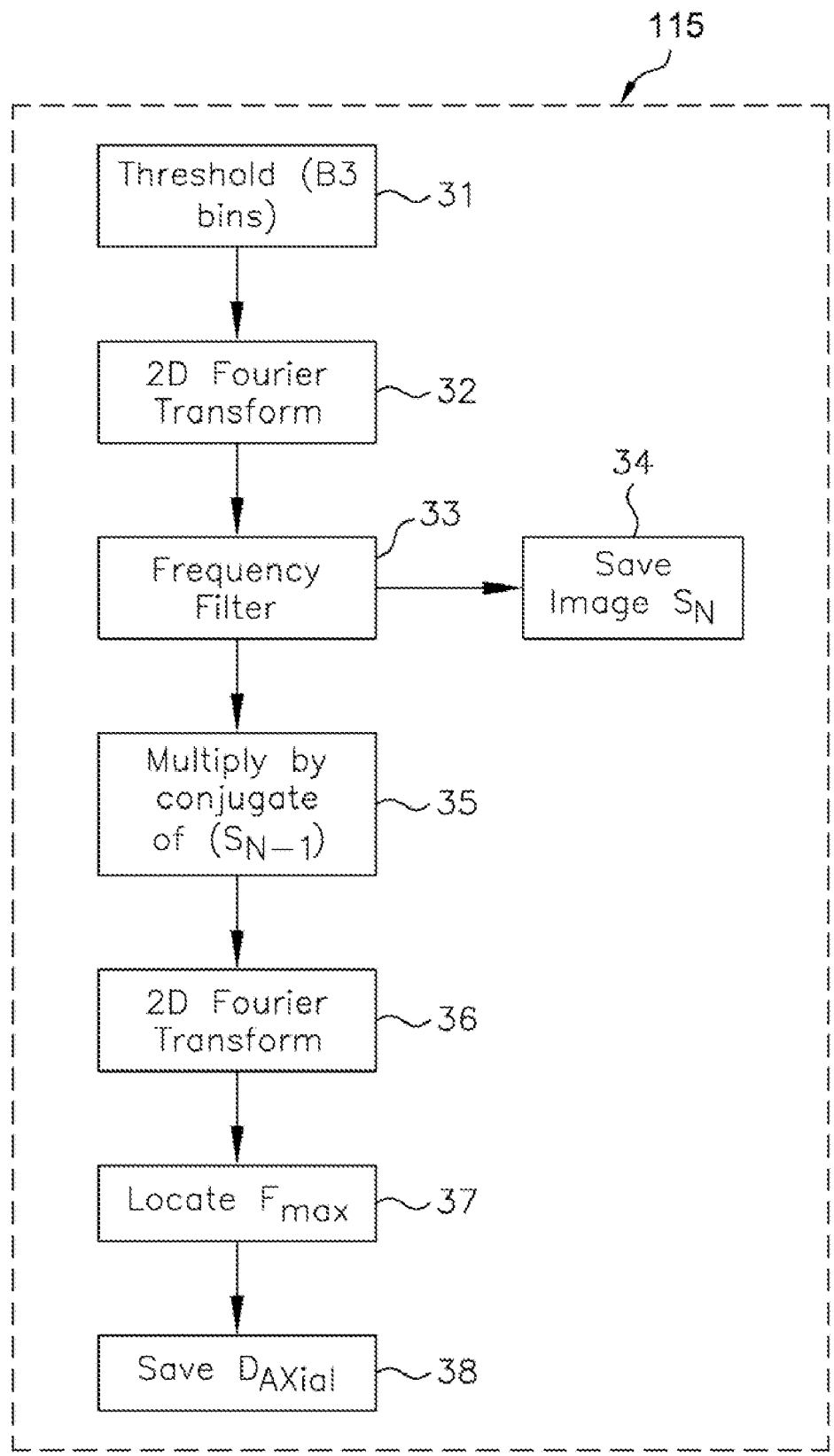
FIG. 3 is a functional block diagram of an axial correction portion of an imaging system employing the example embodiment described in FIG. 1.

Referring now to FIG. 3, a functional block diagram of an axial correction portion of an imaging system employing the example embodiment described in FIG. 1 is shown. The axial correction 115 is performed on all images except the first. A copy of the input image is thresholded at step 31, and then cross-correlated with a thresholded copy of the previous image. The offset is determined as the maximum in the cross-correlation function along the line that corresponds to the difference in the lateral correction for the current perspective [$D_{LAT}(N)$] and the lateral correction for the immediately preceding perspective [$D_{LAT}(N-1)$]. Unlike the lateral correction 114, therefore, the axial correction 115 is an iterative process and thus is subject to cumulative errors.

A copy of the input image is thresholded 31 in the same manner as for the lateral correction, but in this case the number of bins in the histogram is B3. In the present example, B3=2. Thus, all pixels with a gray level greater than the mid-range gray level are set to zero, while those with lower gray levels retain their initial values. For example, an input image with minimum and maximum values of 31 and 190, respectively, will result in a thresholded image identical to the initial one, except that all pixels that were initially brighter than 110 are now zero.

Having thus blacked out the bright pixels, the thresholded image is Fourier-transformed in 2D 32. It is then filtered 33 to eliminate the smallest features, which may produce spurious peaks on the cross correlation. Only spatial frequencies up to 102 cycles/pixel, corresponding to feature sizes of ten pixels or less, are multiplied and pixels at higher spatial frequencies are set to zero. The resulting array is saved 34 as $S_N$ and multiplied 35 by the complex conjugate of $S_{N-1}$, obtained from the preceding image's thresholded copy. A 2D FFT is next applied to the resulting array to find the cross-correlation of the two consecutive, thresholded, low-pass-filtered images. The difference in the lateral offset between the two consecutive images [$D_{LAT}(N)-D_{LAT}(N-1)$] found from the lateral correction step 114 is necessary now, since it is incorrect to find the global maximum of the correlation array. Instead, a local maximum, $F_{MAX}$, must be found in the row that corresponds to [$D_{LAT}(N)-D_{LAT}(N-1)$]. The column containing $F_{MAX}$ is designated $G_{MAX}$. If $G_{MAX}$ is greater than half the padded image dimension (1024, in this example), then its value signifies a negative shift, relative to the preceding image, having a magnitude equal to the zero-padded dimension minus the value of $G_{MAX}$. If $G_{MAX}$ is less than half the zero-padded dimension, then the required shift, relative to the preceding image, is positive and equal to $G_{MAX}$.

As an example, suppose $D_{LAT}(N-1)$=45, while $D_{LAT}(N)$=63. Then $F_{MAX}$ will be found on row 18 of the correlation array (63−45=18). If $F_{MAX}$, the maximum value of row 18, occurs in the fifth column, then $G_{MAX}$=5 and the image must be shifted five pixels to the left of the previous image. If the maximum occurs at row 1019 ($G_{MAX}$=1019), then the image must be shifted five pixels to the right (1024−1019=5) of the previous image, since 1019 is greater than 512.

After $G_{MAX}$ is found, the value of the shift is added to the sum of all the previous axial offsets to determine $D_{AXIAL}$, the cumulative difference from the first acquired image to the current image. The shift may be positive or negative; hence, some images may not require any axial shift. For each image, four values are written to a text file:

1. The position of the upper tube wall, $D_{LAT}$;
2. $C_{MAX}$, the maximum value of the cross-correlation between the current image and the reference image;

3. $G_{MAX}$, the location of $F_{MAX}$ on the appropriate row of the cross-correlation between the current image and the previous image (for the first image, $G_{MAX}=0$);

4. $F_{MAX}$ (for the first image, $F_{MAX}=0$).

The corrected file is generated by cropping the appropriate number of pixels from one or two edges and shifting the remaining pixels by the number cropped. To maintain the original image dimensions (640×480), the spaces at the opposite edges from the cropped edges are replaced by pixels set to the maximum gray level of the original image.

For example, suppose that for one of the images, the maximum gray level is 229, $D_{LAT}$=63, $D_{AXIAL}$=29, and $G_{MAX}$=1022. Then the pixels in the top eight rows (63−55=8) and the left 27 columns (29−1024+1022=27) are deleted from the image. Thus the ninth row of column 28 occupies the upper left corner. Eight rows are added to the bottom of the image, and 28 columns are added to the right of the image; these pixels have gray levels of 229. When these procedures are complete, the 632×453-pixel region in the upper left of the corrected image is identical to the 632×453-pixel region in the lower right of the original image. Both images have dimensions of 640×480.

Another example embodiment incorporates only the axial correction 115 and the writing of the corrected image 116. This embodiment is useful when the walls of the microcapillary tube are not visible and the tube's lateral motion is known to be negligible In yet another embodiment, the tube wall separation is calculated automatically from the first view (N=0). Otherwise it is identical to the embodiment described hereinabove with reference to FIGS. 1–3. In another embodiment of the invention, the separation of the tube walls is determined based on a calculation of their separation in one or more of the images. This is accomplished by using as a reference an image derived from a single bright line, as by a 2D FFT and a complex conjugation. The rows are summed, as in the first embodiment, and the location of the maximum is taken as the location of one wall of the tube relative to its location in the image from which the reference image was derived. The location of the next highest correlation value gives the location of the other tube wall, relative to the first. If desired, the search for this secondary maximum can be restricted to a range whose central location, relative to the first tube wall, is in the vicinity of the presumed tube width. This embodiment also encompasses the possibility of using the single-line reference for all the acquired viewpoints. Such an arrangement may be useful when the tube wall separation is not known, or when the tube's inner walls do not form a circle, as when the tube's inner profile is square is elliptical.

In another embodiment of the invention, the characteristics of the thresholding step may vary based on feedback from the correlation. Such iterative approaches may be employed in the first thresholding step for the lateral correction, in the second thresholding step for the axial correction, or in both. One characteristic that may be varied is the number of divisions or bins used in the histogram. Another characteristic that can be varied is the number of gray levels contained within each histogram bin. For example, the histogram may be based on the square root of the brightness level.

According to a feature of the invention, the output of the method is a cropped copy of the input file, with the uncropped portions shifted vertically and/or horizontally, and with additional blank pixels inserted at one or two of the borders to retain the input image size.

According to a further feature of the invention, the results of the method employed are saved to a digital file, which may be altered and edited using computer word-processing applications. The altered text file may then be used to generate the offsets in the two axes, thus bypassing many of the calculations described above. In this embodiment, the lateral correction procedure of steps 114 through 116 is iterated to find the maximum of $C_{MAX}$. If $C_{MAX}$ has a magnitude less than a critical value $C_{CRIT}$, then the entire procedure is repeated, starting with the thresholding 27, but with the number of bins in the histogram changed from B1 to B2. $C_{MAX}$ is again located 26 and evaluated 28.

Figure 5:
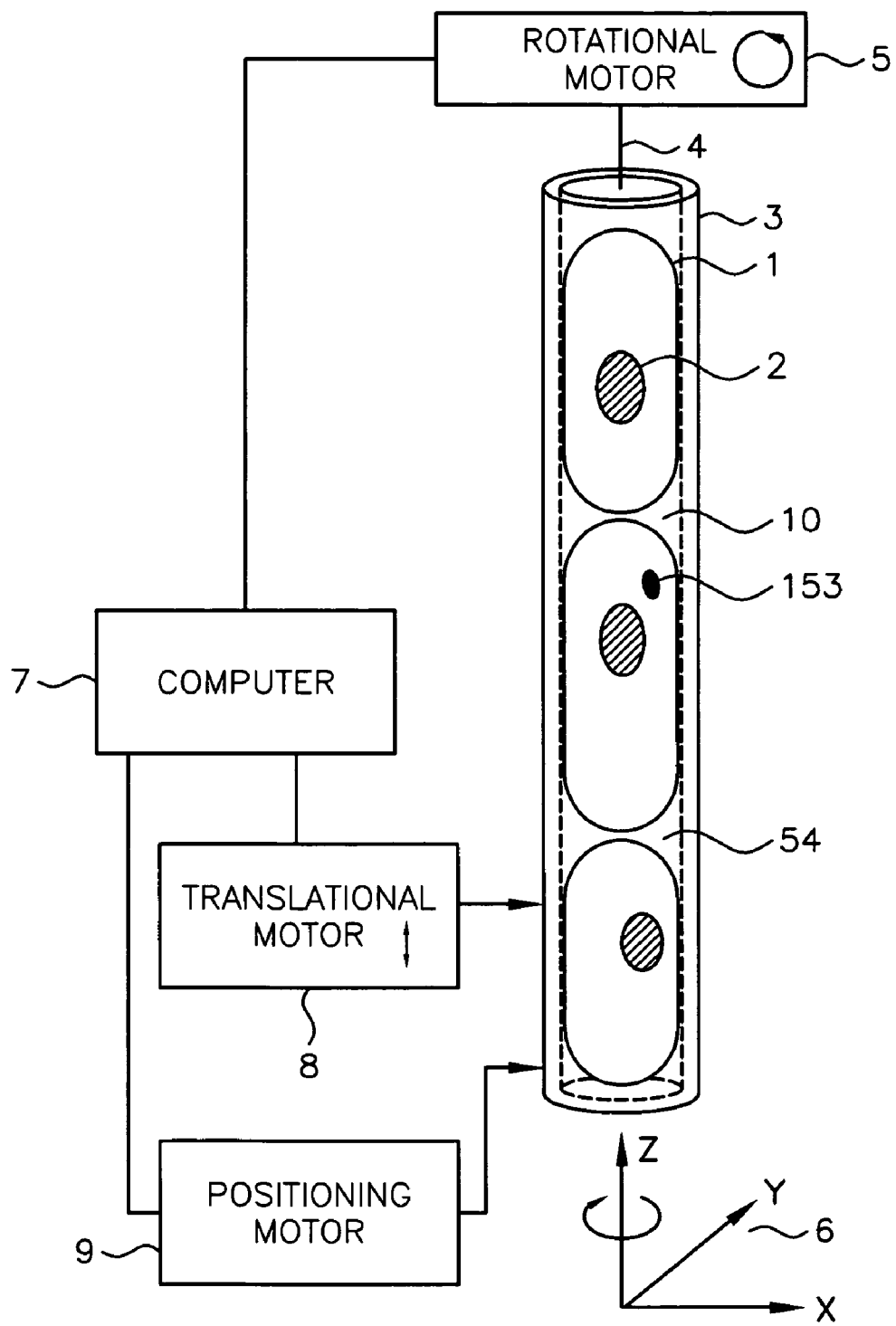
FIG. 5 depicts schematically an optical projection tomographic microscopy (OPTM) system employed in one embodiment of the invention.

Referring now to FIG. 5, there shown schematically is an example illustration of cells packed into a capillary tube as contemplated by an embodiment of the present invention. In this example embodiment, a section of the capillary tube 3 is filled with objects of interest 1, such as cells, that are packed rigidly into the tube. Each of the cells may include a nucleus 2. The capillary tube 3 has a central axis 4 oriented with reference to a coordinate system 6 having coordinates in the x, y and z-directions. In some instances, at least one molecular probe 153 may be bound within the cell. A computer 7 is coupled to provide control signals to a rotational motor 5 and a translational motor 8. It will be recognized that equivalent arrangements of one or more motors, gears or fluidics or other means of generating motion may also be employed to achieve the necessary translational and rotational motion of the capillary tube or other substrate. In some cases, one or more of the motors may be replaced by manual positioning devices or gears or by other means of generating motion such as hydraulic or piezoelectronic devices. The axis of translation is the z-axis, and rotation is around the z-axis. The positioning motor 9 is coupled to move the cell in a plane defined by the x, y-axes, substantially perpendicular to the central axis for the purpose of centration, as necessary.

It will be recognized that the curved surface of the capillary tube will act as a cylindrical lens and that this focusing effect may not be desirable in a projection system. Those skilled in the art will appreciate that the bending of photons by the tube can be eliminated if the spaces between the point source and the tube and between the tube and the detector surfaces are filled with a material 10 whose index of refraction matches that of the capillary tube and that the tube can be optically coupled (with oil or a gel, for example) to the space filling material.

Consider the present example of cells packed into a capillary tube. The cells may preferably be packed single file so that they do not overlap. The density of packing whole cells of about 100 microns in diameter into a capillary tube with diameter less than 100 microns can be roughly 100 cells per centimeter of tube length. For bare nuclei of about 20 microns in diameter, the packing can be roughly 500 nuclei per centimeter of tube length where the tube diameter is proportional to the object size, about 20 microns in this case. Thus, within several centimeters of capillary tube length, a few thousand non-overlapping bare nuclei can be packed. By translating the tube along its central axis 4, motion in the z-direction can be achieved. Moving the tube in the x, y-directions allows objects within the tube to be centered, as necessary, in the reconstruction cylinder of the optical tomography system. By rotating the tube around its central axis 4, a multiplicity of radial projection views can be produced. Moving the tube in the z-direction with constant velocity and no rotation simulates the special case of flow optical tomography.

One advantage of moving a tube filled with cells that are otherwise stationary inside the tube is that objects of interest can be stopped, then rotated, at speeds that permit nearly optimal exposure for optical tomography on a cell-by-cell basis. That is, the signal to noise ratio of the projection images can be improved to produce better images than may be usually produced at constant speeds and direction typical of flow systems. Objects that are not of interest can be moved out of the imaging system swiftly, so as to gain overall speed in analyzing cells of interest in a sample consisting of a multitude of cells. Additionally, the ability to stop on an object of interest, then rotate as needed for multiple projections, nearly eliminates motion artifacts. Still further, the motion system can be guided at submicron movements and can advantageously be applied in a manner that allows sampling of the cell at a resolution finer than that afforded by the pixel size of the detector. More particularly, the Nyquist sampling factor of 2 could be managed by the motion system moving in increments that fill half a pixel width, for example. Similarly, the motion system can compensate for the imperfect fill factor of the detector.

Figure 6A:
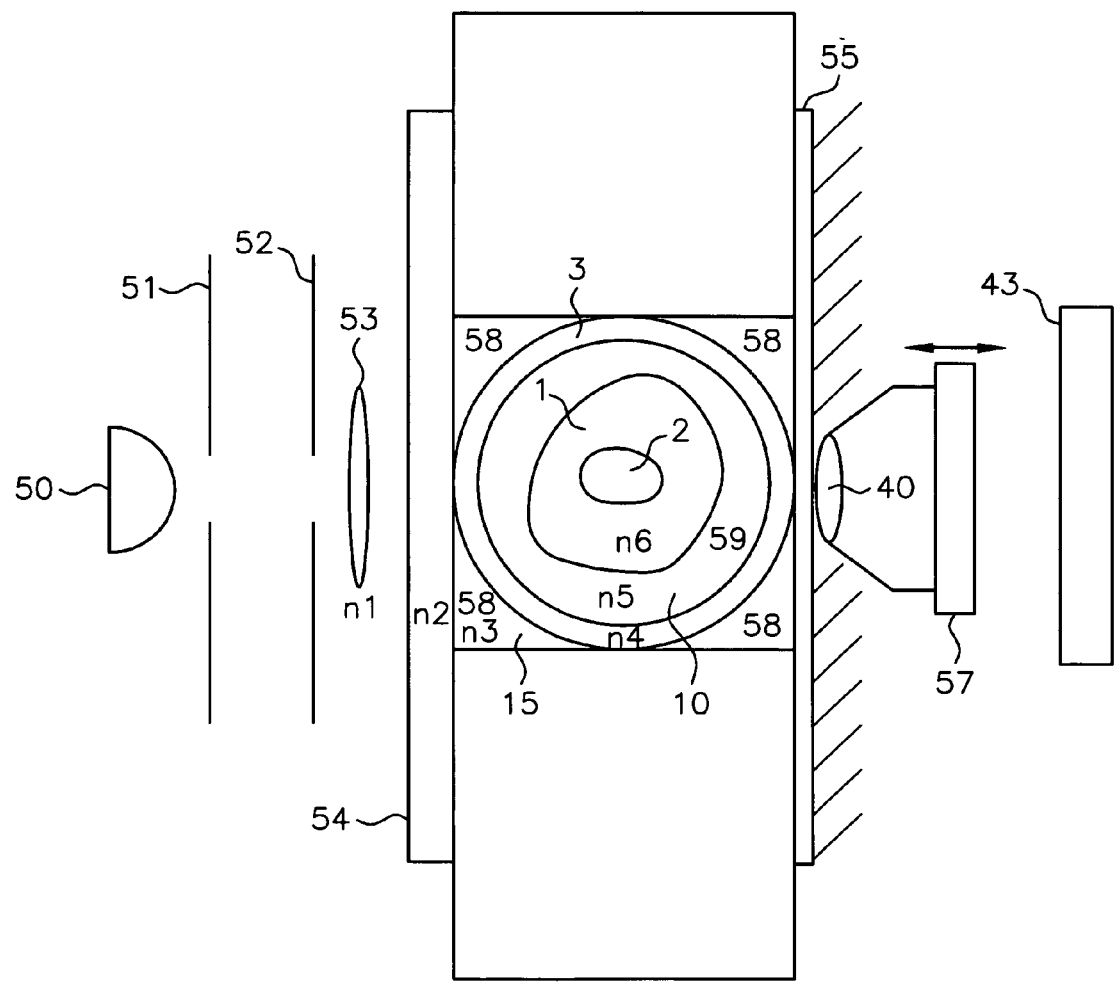
FIG. 6A and FIG. 6B show one embodiment of an optical tomography system incorporating a microscope objective lens mounted on a piezoelectric translation.

Referring now to FIG. 6A, there shown is a close-up view of a single specimen, as for example a single cell, immersed within a medium of optical indexing material. The single specimen is shown within a micro-capillary tube 3 (e.g. one such tube is manufactured by Polymicro Technologies, LLC., AZ, US) that can be rotated for taking multiple projections and an objective lens 40 that can be axially scanned is schematically shown. An illumination source includes a light source 50 that projects light through an aperture 51, a stop 52, and through a condenser lens 53 that is positioned before a microscope slide 54. A micro-capillary tube 3 holds a cell 1 between the slide and a thin coverslip 55. An objective lens 40, preferably an oil-immersion lens, is disposed to receive light passed through the micro-capillary tube 3. The objective lens is translated along the optical axis by an actuator 57 such as a piezoelectric element. The coverslip 55 must be thin enough so that the distance between the center of the micro-capillary tube and the outer surface of the coverslip is smaller than the working distance of the objective lens. The condenser lens 53 is within the index of refraction n, (e.g. air). The slide 54 and coverslip 55 have index of refraction $n_2$. A region 58 surrounding the micro-capillary tube 3 contains index-matching medium 15 such as optical gel or immersion oil, which has index of refraction $n_3$. The micro-capillary tube 3 itself has index of refraction $n_4$. The region 59 surrounding the cell 1 within the micro-capillary tube contains a medium 10 possessing an index of refraction $n_5$. A region 60 within the cell may be filled with the same medium 10, or may differ in its index of refraction $n_6$. It is preferred that $n_3=n_4=n_5=n_6$ (differences must be minimized) between the two flat parallel surfaces formed by slide 54 and coverslip 55 to avoid a cylindrical lens distortion. The image is projected onto a camera 43.

Figure 6B:
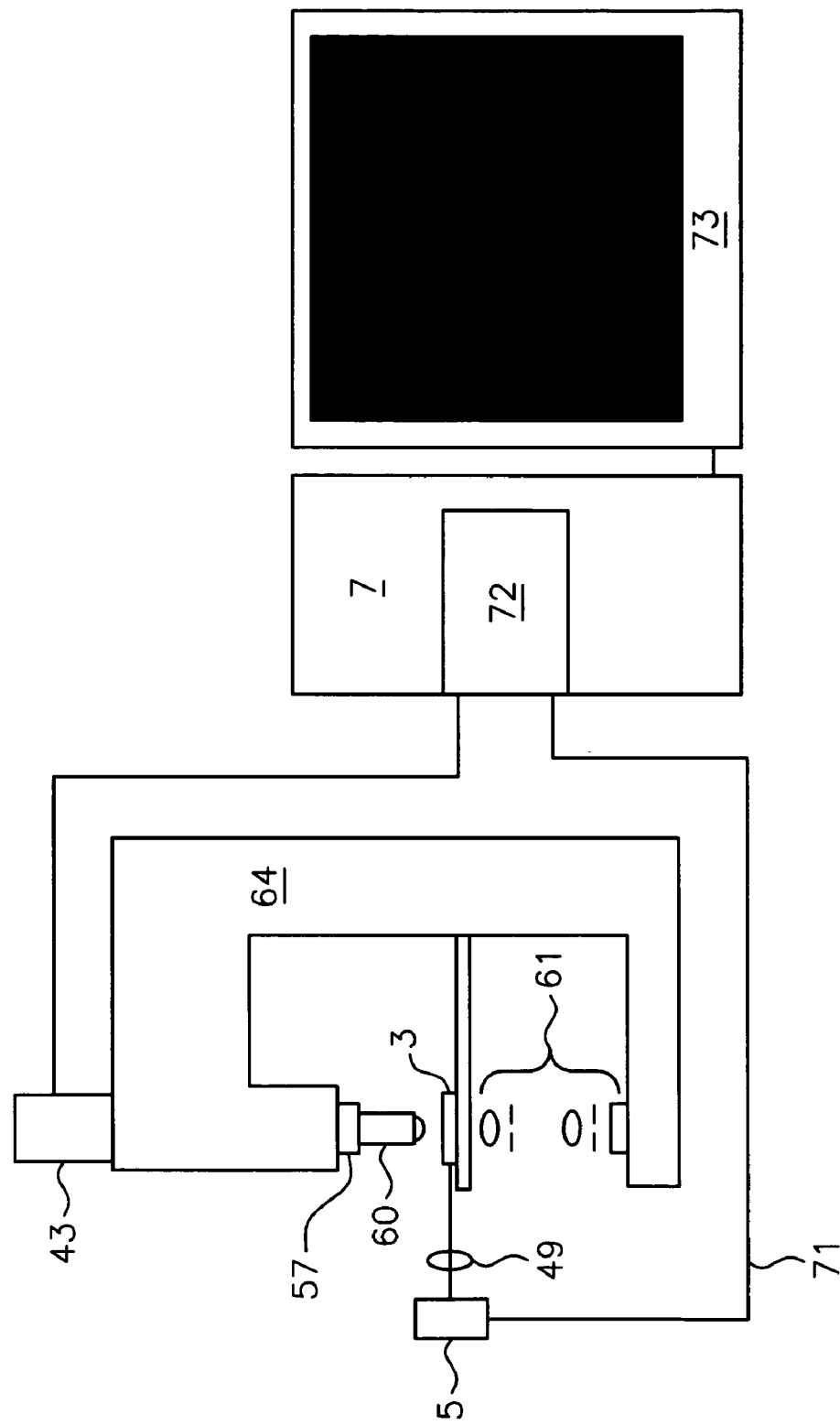

Referring now to FIG. 6A and FIG. 6B, one embodiment of an optical tomography system employed in the present invention, incorporating a microscope objective lens mounted on a piezoelectric translation device is schematically shown. The piezoelectric transducer 57 is used to move an objective lens 60 an axial distance of about 40 microns or more. In one useful embodiment, a micro-objective positioning system provides a suitable actuator 57, which is driven up and down along the z axis of tube coordinate system 6. In this embodiment, it may be used with a high numerical aperture objective, mounted on an standard transmission microscope 64 with a video camera 43 attached and a computer-controlled light source and condenser lens assembly 61. The computer-controlled condenser and light source 50 may advantageously be a light source including one or more incandescent bulbs, an arc lamp, a laser, or a light emitting diode. Computer control signals 70 are linked to the computer-controlled condenser and light source 50 for controlling light modulation.

The output from the camera 43 is stored in a computer memory 72. A microcapillary tube 3 containing the specimen can be translated along the x or y axes of tube coordinate system 6. In addition, the microcapillary tube 3 can be rotated about its "θ" axis 49, via a rotational motor 5 that can be computer-controlled. As used herein microcapillary tube is defined as a capillary tube having a diameter where the field of view for microscopic imaging is comparable to the capillary tube diameter. In an example embodiment the rotational motor 5 is controlled by control signals 71 as provided by the computer 7. For high speed applications other controls may be added in order to reduce vibrations during an axial scan. The acquired image may be displayed on monitor 73.

Figure 7:
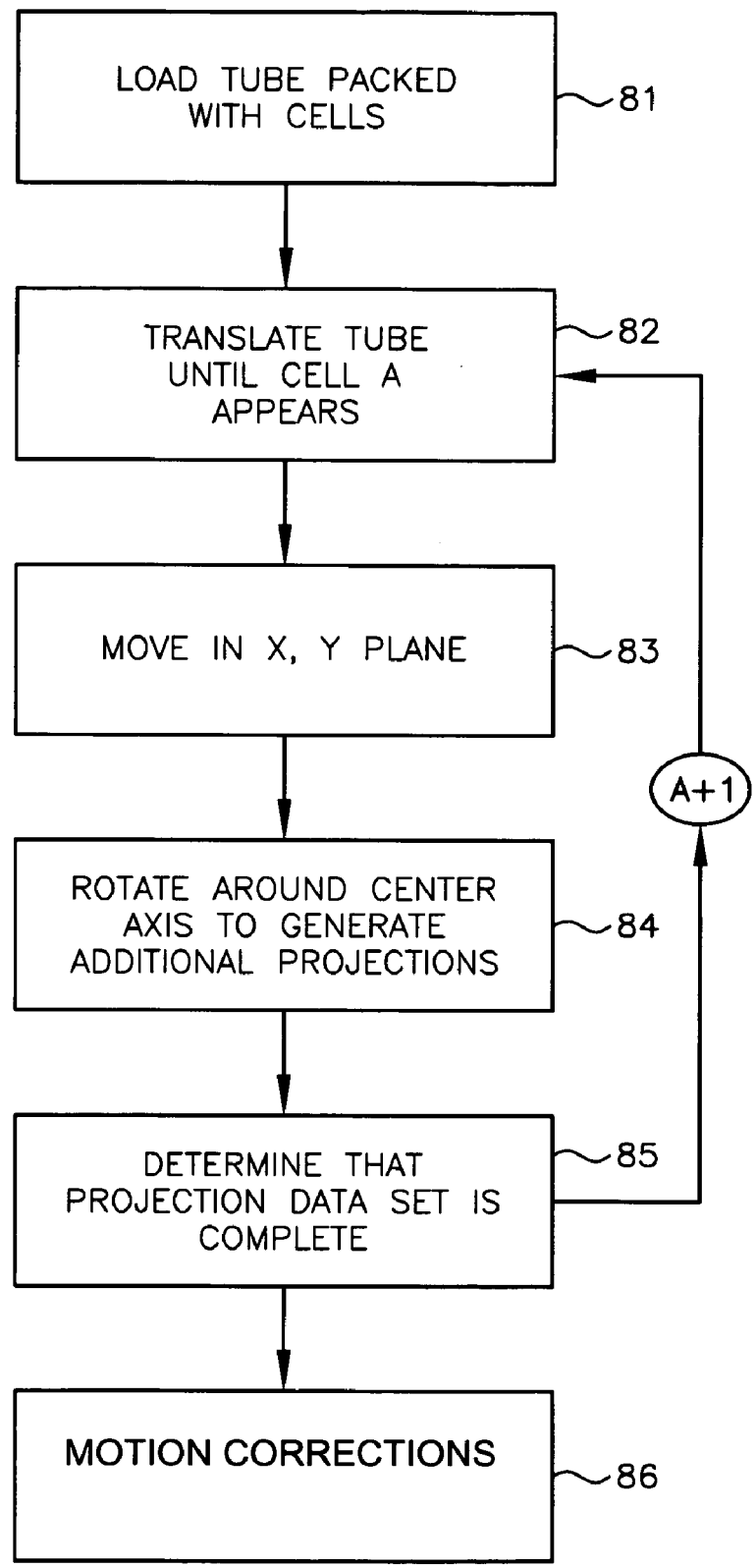
FIG. 7 shows an example flow diagram illustrating a process for acquiring images used in three-dimensional (3D) image reconstruction as contemplated by an embodiment of the present invention.

Referring now to FIG. 7, an example flow diagram illustrating a process for acquiring images used in three-dimensional (3D) image reconstruction as contemplated by an embodiment of the present invention is shown. As contemplated by one example of the present invention, a 3D image reconstruction process includes the steps of loading the tube packed with cells at step 81, translating the tube until the first cell of interest has been located at step 82, centering the cell of interest, as necessary, at step 83, generating a set of projections at each different rotation angle at step 84, determining when the data set is complete at step 85, and repeating the process from steps 82 through 85 until all cells of interest have been scanned. At step 86 motion corrections are made. The process may be implemented in a computer software program executed by a personal computer such as computer 7, for example.

Figure 8:
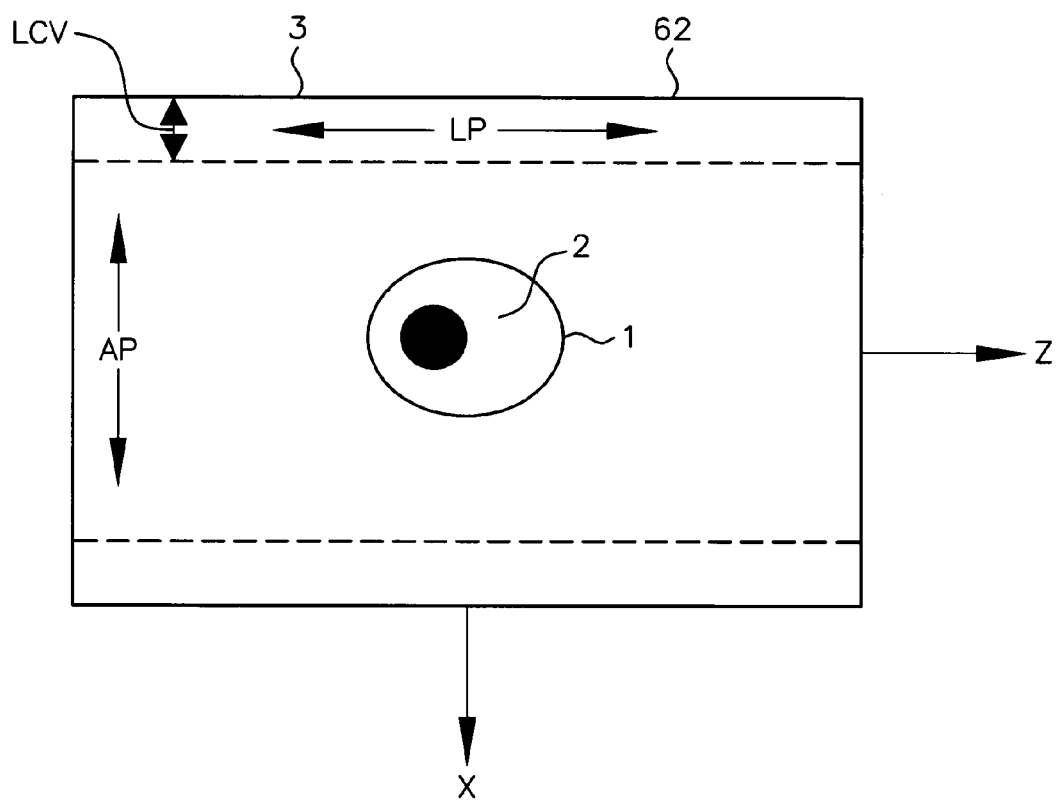
FIG. 8 shows schematically an example of motion correction offsets for use in a three-dimensional (3D) image reconstruction as contemplated by an embodiment of the present invention.

Referring now to FIG. 8, there shown schematically is an example of motion correction offsets for use in a three-dimensional (3D) image reconstruction as contemplated by an embodiment of the present invention. Motion correction is applied to find the lateral position of an object of interest 1, such as a cell or nucleus 2, contained in a capillary tube 3 having a capillary tube wall 62. The lateral offset is the error along the longer image dimension (640 pixels), perpendicular to the tube axis, Z. The axial offset is the error along the shorter image dimension (480 pixels), parallel to the tube axis Z. The object of interest 1 has a lateral position LP and an axial position AP. As images are acquired from various points of view, motion correction is applied in order to allow reconstruction of the object of interest with identical features maintained in the same plane in the various views.

EXAMPLE SOFTWARE CODE DESCRIPTION

Source Code

Below is the text of an example of source code for implementing one embodiment of the method of the invention for motion correction. The executable file (regcorr.exe) is built from two header files (rrahn.h and regcorr.h) and four C++ files (fileinfo.cpp, nr-fft.cpp, multiplycomplexvalues.cpp, and regcorr2.cpp), linked by project regcorr.ide. The project was compiled by Borland C++ 5.01, set for "Win32 Console" mode, and using the static class library framework. The executable file size is roughly 60 kB. (Programs, "regcorr.exe" and "regcorr_no_lateral.exe," differ only in whether they provide the option of calculating the lateral offset and writing it to a text file. Both programs can also skip the calculations and instead read the offsets from a text file.)

*A.1    rrahn.h (38 lines)*

```
#include <math.h>
#include <malloc.h>
#include <fstream.h>
#include <dos.h>
#include <iostream.h>
#include <stdio.h>
#include <conio.h>
#include <complex.h>
#pragma hdrstop
#pragma package(smart_init)

//using namespace std;

#define pi_const 3.14159265358979323846
define unsigned int template<class T>
inline const T SQR(const T a) {return a*a;} inline float pow(float x, double y) {return pow(double(x), y);}
inline float pow(double x, float y) {return pow(x, double(y));}
inline float atan2(float x, double y) {return atan2(double(x), y);}
inline float atan2(double x, float y) {return atan2(x, double(y));}
```

```
template <class T>
inline void SWAP(T &a, T &b)
    {T dum=a; a=b; b=dum;} define SwapFFT SWAP

//void wait()
//{
//    while( !kbhit() );
//    return;
//}
#define wait while(!kbhit()); return;

unsigned *UIivector(unsigned, unsigned);
```

A.2  regcorr.h (40 lines)

```
#include "rrahn.h"
#pragma hdrstop
#pragma package(smart_init)

const unsigned ImageDimX = 640;
const unsigned ImageDimZ = 480;
const unsigned BigDimX = 1024;   //BigDims for FFT routine--must be a power of 2
const unsigned BigDimZ = 1024;
const unsigned NumHistoBins = 20;
const unsigned WallSpacingMin = 505, WallSpacingMax = 565;

extern unsigned FileYear, FileMonth, FileDay, FileSet,
NumPerspectives, CurrentPerspective, BinHist[NumHistoBins];
extern int SliceNumber;
extern char filenameIn[64];
extern char ProcessedFilenameOut[64];
extern float RawImage[ImageDimX*ImageDimZ];
extern double ShiftedImage[BigDimX*BigDimZ*2],
ShiftedImageNew[BigDimX*BigDimZ*2];
extern double TemplateImage[BigDimX*BigDimZ*2],
TemplateImageNew[BigDimX*BigDimZ*2];
extern int ShiftX;
extern int ShiftZ;
extern double MaxVal, MinVal;
extern float BinVal[ImageDimX*ImageDimZ];
extern unsigned MaxBin, MaxHisto;
extern int BigDims[2];
extern char* DirectoryName;
extern unsigned WallEdge1, WallEdge2, WallSpacing;
extern double MinValDev1, MinValDev2, MaxValCorr, MaxValCorr2;
extern unsigned MinDevIndex, MaxCorrIndex, MaxCorrIndex2;
extern unsigned MinDevIndexOld;
```

```cpp
extern double ShiftedMag[2*BigDimX*BigDimZ];
extern unsigned ppmax;
extern float CriticalValue;

void MultiDimFFT(double[],int[],int, int);
void FindDeviation();
void GetFileInfo();
void WriteCorrectedImage(double[]);
void    MultiplyComplexValues(double[],    double[],    double[],
unsigned, unsigned,unsigned, unsigned);
void BasicFFT(float[], unsigned long, int);
void MakeFileName(char*, unsigned, unsigned);
```

*A.3    fileinfo.cpp (50 lines)*

```cpp
#include "rrahn.h"

unsigned NumPerspectives;
unsigned FileYear, FileMonth, FileDay, FileSet;

void GetFileInfo()
{
   cout << "Year (YY, 3 or 4):   ";
   cin >> FileYear;
   while(FileYear != 3 && FileYear != 4)
   {
      cout << "Year (YY, 3 or 4):   ";
      cin >> FileYear;
   } cout << "Month (MM):    ";
//    gets(FileYear);
   cin >> FileMonth;
   while(FileMonth>12)
   {
      cout << "Month (MM):    ";
      cin >> FileMonth;
   } cout << endl << "Day (DD):   ";
   cin >> FileDay;
   while(FileDay>31)
   {
      cout << "Day (DD):   ";
      cin >> FileDay;
   } cout << endl << "Set (1-99):   ";
   cin >> FileSet;
   while(FileSet>99)
   {
```

```
      cout << "Set (1-99):  ";
      cin >> FileSet;
   }
      cout << endl;

cout << "Number of Perspectives (1-255):  ";
   cin >> NumPerspectives;
   while(NumPerspectives>255 || NumPerspectives<1)
   {
      cout << "Number of Perspectives (1-255):  ";
      cin >> NumPerspectives;
   }
   return;
}
```

A.4  nr-fft.cpp (221 lines)

```
#include "rrahn.h"

/*this function corresponds to program "four1" in "Numerical
Recipes in C" */
void BasicFFT(float FFTdata[], unsigned long FFTnn, int FFTisign)
/* Replaces FFTdata[1..2*FFTnn] by its discrete Fourier
transform, if FFTisign
// is input as 1; or by its inverse discrete Fourier transform
times FFTnn if
// FFTisign is input as -1.        */
{
   unsigned long FFTm, FFTistep;
   unsigned long FFTmmax = 2;
   double FFTwtemp, FFTwr, FFTwpr, FFTwpi, FFTwi, FFTtheta;
//Double precision
   float FFTtempr, FFTtempi;                                //for
the trig
   unsigned     long     FFTn     =     FFTnn     <<     1;
//recurrences
   unsigned long FFTj = 1;
   for(unsigned long jj = 1; jj < FFTn; jj += 2)    //The is the
bit-reversal
   {                                                //section
      if(FFTj > jj)
      {
         SwapFFT(FFTdata[FFTj], FFTdata[jj]);        //Exchange
the two complex
         SwapFFT(FFTdata[FFTj+1], FFTdata[jj+1]);  //numbers
      }
         FFTm = FFTn >> 1;
      while(FFTm >= 2 && FFTj > FFTm)
      {
         FFTj -= FFTm;
         FFTm = FFTm >> 1;
```

```
            }
        FFTj += FFTm;
        }
/*Here begins the Danielson-Lanczos section of the routine*/
        while(FFTn > FFTmmax)                   /* Outer loop executed
log2(FFTnn) times) */
    {
        FFTistep = FFTmmax << 1;                /* Initialize the trig
recurrence */
        FFTtheta = FFTisign*(2.0*pi_const/FFTmmax);
        FFTwtemp = sin(0.5*FFTtheta);
        FFTwpr = -2.0*FFTwtemp*FFTwtemp;
        FFTwpi = sin(FFTtheta);
        FFTwr = 1.0;
        FFTwi = 0.0;
        /* Here are the two nested inner loops,      //
        //which include the Danielson-Lanczos formula */
        for(FFTm = 1; FFTm < FFTmmax; FFTm += 2)
        {
            for(unsigned long jj = FFTm; jj <= FFTn; jj +=
FFTistep)
            {
                FFTj = jj + FFTmmax;
                FFTtempr       =       FFTwr*FFTdata[FFTj]       -
FFTwi*FFTdata[FFTj+1];
                FFTtempi       =       FFTwr*FFTdata[FFTj+1]      +
FFTwi*FFTdata[FFTj];
                FFTdata[FFTj] = FFTdata[jj] - FFTtempr;
                FFTdata[FFTj+1] = FFTdata[jj+1] - FFTtempi;
                    FFTdata[jj] += FFTtempr;
                    FFTdata[jj+1] += FFTtempi;
            }
            FFTwtemp = FFTwr;
            FFTwr = FFTwtemp*FFTwpr - FFTwi*FFTwpi + FFTwr;   /* Trig
recurrence */
            FFTwi = FFTwi*FFTwpr + FFTwtemp*FFTwpi + FFTwi;
            }
        FFTmmax = FFTistep;
    }
    return;
}

/* This function corresponds to program "realft" in "Numerical
Recipes in C" */
void ApplyOneDimFFT(float FFTdata[], unsigned long FFTn, int
FFTisign)
/* Calculates the Fourier Transform of a set of 2*FFTn real-
valued data points.
//Replaces this data (which is stored in FFTdata[1..2*FFTn] by
the positive
//frequency half of its Fourier Transform. The real-valued first
and last
```

```
//components are returned as elements FFTdata[1] and FFTdata[2],
respectively.
//FFTn must be a power of 2.  This routine also calculates the
inverse transform
//of a complex data array if it is the transform of real data
(this means that
//F(-f)=|F(f)|*.  In this case the result must be multiplied by
1/FFTn.              */
{
    unsigned long FFTi, FFTi1, FFTi2, FFTi3, FFTi4, FFTnp3;
    float FFTc1=0.5, FFTc2, FFTh1r, FFTh1i, FFTh2r, FFTh2i;
    double FFTwr, FFTwi, FFTwpr, FFTwpi, FFTwtemp, FFTtheta;
       //Double precision
    FFTtheta = pi_const/(double)(FFTn>>1);                    //for
trig recurrences
    void BasicFFT(float FFTdata[], unsigned long FFTnn, int
FFTisign);

if (FFTisign == 1)
    {
       FFTc2 = -0.5;
       BasicFFT(FFTdata, FFTn>>1, 1);        //Forward transform
    }
    else
    {
       FFTc2 = 0.5;                           //Otherwise do an
inverse transform
       FFTtheta = -FFTtheta;
    }
    FFTwtemp = sin(0.5*FFTtheta);
    FFTwpr = -2.0*FFTwtemp*FFTwtemp;
    FFTwpi = sin(FFTtheta);
    FFTwr = 1.0 + FFTwpr;
    FFTwi = FFTwpi;
    FFTnp3 = FFTn + 3;
    for (FFTi=2; FFTi<=(FFTn>>2); FFTi++)    //Case FFTi=1 done
separately below
    {
       FFTi1 = FFTi + FFTi - 1;
       FFTi2 = 1 + FFTi1;
       FFTi3 = FFTnp3 - FFTi2;
       FFTi4 = 1 + FFTi3;
       FFTh1r = FFTc1*(FFTdata[FFTi1] + FFTdata[FFTi3]);   //The
two separate
       FFTh1i  =   FFTc1*(FFTdata[FFTi2]  -   FFTdata[FFTi4]);
//transforms are
       FFTh2r  =  -FFTc2*(FFTdata[FFTi2]  +   FFTdata[FFTi4]);
//separated out of data
       FFTh2i = FFTc2*(FFTdata[FFTi1] - FFTdata[FFTi3]);
       FFTdata[FFTi1]  =  FFTh1r  +  FFTwr*FFTh2r  -  FFTwi*FFTh2i;
//Here they are
```

```
        FFTdata[FFTi2]   =   FFTh1i   +   FFTwr*FFTh2i   +   FFTwi*FFTh2r;
//recombined to
        FFTdata[FFTi3] = FFTh1r - FFTwr*FFTh2r + FFTwi*FFTh2i;
//form the true
        FFTdata[FFTi4]    =    -FFTh1i    +    FFTwr*FFTh2i    +
FFTwi*FFTh2r; //transform of the
     FFTwtemp                    =                    FFTwr;
//original real data
     FFTwr = FFTwtemp*FFTwpr - FFTwi*FFTwpi + FFTwr;        //The
recurrence
     FFTwi = FFTwi *FFTwpr + FFTwtemp*FFTwpi + FFTwi;
   }
   if(FFTisign == 1)
   {
     FFTh1r = FFTdata[1];
     FFTdata[1] = FFTh1r + FFTdata[2];         //Squeeze the first
and last data
     FFTdata[2] = FFTh1r - FFTdata[2];         //together to get
them all within
   }                                            //the original
array
   else
   {  //This is the inverse transform
     FFTh1r = FFTdata[1];
     FFTdata[1] = FFTc1*(FFTh1r + FFTdata[2]);
     FFTdata[2] = FFTc1*(FFTh1r - FFTdata[2]);
     BasicFFT(FFTdata, FFTn>>1, -1);
     for(unsigned jj=0; jj<FFTn; jj++)
     {
        FFTdata[jj+1] = 2.0*FFTdata[jj+1]/FFTn;
     }
   }
}

/*This function corresponds to function "fourn" in Numerical
Recipes in C
It replaces "data[]" by its "ndim"-dimensional discrete Fourier
transform, if
"isign" is input as 1.  "nn[1...ndim]" is an integer array
containing the lengths
of each dimension (number of complex values), which MUST all be
powers of 2.
"data[]" is a real array of length twice the product of these
lengths, in which
the data are stored as in a multidimensional complex array: real
and imaginary
parts of each element are in consecutive locations, and the
rightmost index of the
array increases most rapidly as one proceeds along "data[]." For
a two-dimensional
``` array, this is equivalent to storing the array by rows.  If "isign" is input as
-1, "data[]" is replaced by its inverse transform times the product of the lengths
of all dimensions.
*/

```
void MultiDimFFT(double data[], int nn[], int ndim, int isign)
{
      int i1, i2, i3, i2rev, i3rev, ip1,ip2, ip3, ifp1, ifp2;
   int ibit, idim, k1, k2, n, nprev, nrem, ntot;
   double tempi, tempr;
   double theta, wi, wpi, wpr, wr, wtemp;

ntot = 1;
   for(idim=1; idim<=ndim; idim++)     //Compute total number of complex values.
      ntot *= nn[idim];
   nprev = 1;
   for(idim=ndim; idim>=1; idim--)           //Main loop over the dimensions.
   {
      n=nn[idim];
       nrem = ntot/(n*nprev);
       ip1 = nprev << 1;
       ip2 = ip1*n;
       ip3 = ip2*nrem;
       i2rev = 1;
       for(i2=1; i2<=ip2; i2+=ip1)    //This is the bit-reversal
                                      section of the routine.
       {
          if(i2<i2rev)
         {
           for(i1=i2; i1<=(i2+ip1-2); i1+=2)
            {
                for(i3=i1; i3<=ip3; i3+=ip2)
              {
                i3rev = i2rev+i3-i2;
                   SwapFFT(data[i3], data[i3rev]);
                   SwapFFT(data[i3+1], data[i3rev+1]);
              }
           }
         }
         ibit = ip2 >> 1;
         while( (ibit>=ip1) && (i2rev>ibit) )
         {
           i2rev -= ibit;
             ibit >>= 1;
         }
         i2rev += ibit;
      }
        ifp1 = ip1;              //Here begins the Danielson-Lanczos section of the routine.
```

```
    while(ifp1<ip2)
    {
        ifp2 = ifp1 << 1;
        theta = isign*2*pi_const/(ifp2/ip1);    //Initialize for
the trig recurrence.
        wtemp = sin(0.5*theta);
        wpr = -2.0*SQR(wtemp);
        wpi = sin(theta);
        wr = 1.0;
        wi = 0.0;
        for(i3=1; i3<=ifp1; i3+=ip1)
        {
          for(i1=i3; i1<=(i3+ip1-2); i1+=2)
            {
                for(i2=i1; i2<=ip3; i2+=ifp2)
                {
                  k1 = i2;
//Danielson-Lanczos formula.
                  k2 = k1+ifp1;
                  tempr = wr*data[k2] - wi*data[k2+1];
                  tempi = wr*data[k2+1] + wi*data[k2];
                  data[k2] = data[k1] - tempr;
                  data[k2+1] = data[k1+1] - tempi;
                  data[k1] += tempr;
                  data[k1+1] += tempi;
                }
            }
            wtemp = wr;
            wr = wtemp*wpr - wi*wpi + wr;
//Trigonometric recurrence.
            wi = wi*wpr + wtemp*wpi + wi;
        }
        ifp1 = ifp2;
    }
    nprev *= n;
  }
  return;
}
```

*A.5   multiplycomplexvalues.cpp (30 lines)*

```
#include "rrahn.h"

void MultiplyComplexValues(double MCV1[], double MCV2[], double MCV3[], unsigned MCVDim1,
                                        unsigned MCVDim2, unsigned MaxFrequency1, unsigned MaxFrequency2)
{
    for(unsigned mm=0; mm<MCVDim2; mm++)
    {
        for(unsigned nn=0; nn<MCVDim1; nn++)
```

```
    {
        if( (mm>=MaxFrequency2 && mm<MCVDim2-MaxFrequency2)
                                || (nn>=MaxFrequency1 && nn<MCVDim1-MaxFrequency1) )
        {
            MCV3[2*nn*MCVDim2+2*mm] = (double) 0.0;
            MCV3[2*nn*MCVDim2+2*mm+1] = (double) 0.0;
        }
        else
        {
            MCV3[2*nn*MCVDim2+2*mm]                         =       (double)
(MCV1[2*nn*MCVDim2+2*mm]

*MCV2[2*nn*MCVDim2+2*mm]

+ MCV1[2*nn*MCVDim2+2*mm+1]

*MCV2[2*nn*MCVDim2+2*mm+1]);
                    MCV3[2*nn*MCVDim2+2*mm+1]                       =
(double)(MCV2[2*nn*MCVDim2+2*mm]

*MCV1[2*nn*MCVDim2+2*mm+1]                                -
MCV2[2*nn*MCVDim2+2*mm+1]

*MCV1[2*nn*MCVDim2+2*mm]);
        }
    }
}
return;
}
```

A.6  regcorr2.cpp (374 lines)

```
#include <strstrea.h>
#include "regcorr.h"

//unsigned     FileYear,     FileMonth,     FileDay,     FileSet,
NumPerspectives;
unsigned CurrentPerspective;
unsigned BinHist[NumHistoBins];
int SliceNumber;
char filenameIn[64];
char ProcessedFilenameOut[64], IndexFilenameOut[64];
float RawImage[ImageDimX*ImageDimZ];
double ShiftedImage[BigDimX*BigDimZ*2];
double                              TemplateImage[BigDimX*BigDimZ*2],
TemplateImageNew[BigDimX*BigDimZ*2];
double OneLine[BigDimX*BigDimZ*2];
float LateralSum[2*BigDimX];
double MaxVal, MinVal;
```

```
float BinVal[ImageDimX*ImageDimZ];
unsigned MaxBin, MaxHisto, MinDevIndexOld;
int BigDims[2], SmallDims[2];
unsigned MaxCorrIndex, WallEdge1, WallEdge2;
double MaxValCorr;
double ShiftedMag[2*BigDimX*BigDimZ];
char *DirectoryName = "E:\\VisionGate\\Projection Images\\";
unsigned nnc, WallOld1, WallOld2;
float LateralMax1 = 0, LateralMax2 = 0;
float MaxValOld, MinValOld;
unsigned SecondSeg = 2;
unsigned FirstSeg = 20;
unsigned CorrectedFile[4*360];
float RedoLateralCorrection = 2.2e17;
int CumulativeShift = 0;

void ReadUncorrectedImage(unsigned RUI1)
{
    MaxValOld = MaxVal;
    MinValOld = MinVal;
        MaxVal = 0;
    MinVal = 1e22;
    MakeFileName(filenameIn, RUI1,2);
    fstream RawFile(filenameIn,ios::in);
    cout << filenameIn << endl;
        for(unsigned mm=0; mm<ImageDimZ; mm++)
    {
        for(unsigned nn=0; nn<ImageDimX; nn++)
         {
            RawFile >> (float)RawImage[nn*ImageDimZ+mm];
                if(RawImage[nn*ImageDimZ+mm]<MinVal)
              MinVal = RawImage[nn*ImageDimZ+mm];
            if(RawImage[nn*ImageDimZ+mm]>MaxVal)
             MaxVal = RawImage[nn*ImageDimZ+mm];
             }
    }
    RawFile.close();
        return;
} void CopyRawImage(double CRI1[])
{
      for(unsigned mm=0; mm<BigDimZ; mm++)
            for(unsigned nn=0; nn<BigDimX; nn++)
    {
            CRI1[2*nn*BigDimZ + 2*mm+1] = 0;
         CRI1[2*nn*BigDimZ + 2*mm] = 0;
            if(mm<ImageDimZ && nn<ImageDimX)
                  (double)    CRI1[2*nn*BigDimZ    +    2*mm]    =
RawImage[nn*ImageDimZ+mm];
      }
    return;
```

```
} void MakeOneLine()
{
    for (unsigned jj=0; jj<ImageDimZ; jj++)
    {
            OneLine[2*jj] = 65535;
            OneLine[2*jj+2*530*BigDimX] = 65535;
    }
    MultiDimFFT(OneLine-1, BigDims-1, 2, 1);
    return;
} void MakeHistogram(double MHdata[], unsigned MHBins)
{
    if(MHBins>NumHistoBins)
       MHBins = NumHistoBins;
    MaxBin = 0;
    MaxHisto = 0;
    for(unsigned jj=0; jj<NumHistoBins; jj++)
       BinHist[jj] = 0;
    for(unsigned mm=0; mm<ImageDimZ; mm++)
    {
       for(unsigned nn=0; nn<ImageDimX; nn++)
       {
            BinVal[nn*ImageDimZ+mm]
(int)MHBins*(RawImage[nn*ImageDimZ+mm]

-MinVal)/(MaxVal-MinVal);
         if(BinVal[nn*ImageDimZ+mm] >= MHBins)
            BinVal[nn*ImageDimZ+mm] = MHBins - 1u;
         if(BinVal[nn*ImageDimZ+mm] <= 0)
            BinVal[nn*ImageDimZ+mm] = 0u;
         BinHist[(int)BinVal[nn*ImageDimZ+mm]] += 1u;
       }
    }
    for(unsigned jj=0; jj<MHBins; jj++)
    {
      if(BinHist[jj] > MaxHisto)
      {
           MaxHisto = BinHist[jj];
           MaxBin = jj;
      }
    }
    for(unsigned jj=0; jj<2*BigDimX*BigDimZ; jj++)
       MHdata[jj] = 0;
    for(unsigned mm=0; mm<ImageDimZ; mm++)
    {
       for(unsigned nn=0; nn<ImageDimX; nn++)
       {
           if(BinVal[nn*ImageDimZ+mm] < MaxBin)
```

```
                MHdata[2*nn*BigDimZ        +         2*mm]         =
RawImage[nn*ImageDimZ+mm];
        }
    }
    return;
} void LateralCorrection(unsigned LC1)
{
    MakeHistogram(ShiftedImage,LC1);
    MultiDimFFT(ShiftedImage-1, BigDims-1, 2, 1);
    MultiplyComplexValues(ShiftedImage, OneLine, TemplateImageNew,
BigDimX, BigDimZ,
                                                    BigDimX, BigDimZ);
    for(unsigned mm=0; mm<BigDimX; mm++)
    {
       LateralSum[2*mm] = 0;
        LateralSum[2*mm+1] = 0;
        for(unsigned nn=0; nn<BigDimZ; nn++)
        {
            LateralSum[2*mm]                                        +=
TemplateImageNew[2*mm*BigDimZ+2*nn];
                LateralSum[2*mm+1]                                  +=
TemplateImageNew[2*mm*BigDimZ+2*nn+1];
        }
    }
    BasicFFT(LateralSum-1, BigDimX, -1);
    LateralMax1 = 0;
    for(unsigned jj=0; jj<110; jj++)
    {
       if(LateralSum[2*jj] > LateralMax1)
       {
           WallEdge1 = jj;
            LateralMax1 = LateralSum[2*jj];
       }
    }
    WallEdge2 = WallEdge1+530;
        return;
} void AxialCorrection(unsigned AC1)
{
    MaxValCorr = 0.0;
    MaxCorrIndex = 0;
    MakeHistogram(ShiftedImage,AC1);
    for(unsigned jj=0; jj<2*BigDimZ*BigDimX; jj++)
    {
       if(ShiftedImage[jj]>0)
            ShiftedImage[jj] = MaxVal+MinVal-ShiftedImage[jj];
        if(TemplateImage[jj]>0)
            TemplateImage[jj]        =        MaxValOld+MinValOld-
TemplateImage[jj];
```

```
    }
    MultiDimFFT(TemplateImage-1, BigDims-1, 2, 1);
    MultiDimFFT(ShiftedImage-1, BigDims-1, 2, 1);
    MultiplyComplexValues(ShiftedImage,               TemplateImage,
TemplateImageNew, BigDimX, BigDimZ,
                                        BigDimX/10, BigDimZ/10);
    MultiDimFFT(TemplateImageNew-1, BigDims-1, 2, -1);
    if( MinDevIndexOld > (WallEdge1+WallEdge2)/2 )
       nnc = BigDimX + (WallEdge1+WallEdge2)/2 - MinDevIndexOld;
    else
        nnc = (WallEdge1+WallEdge2)/2 - MinDevIndexOld;
    for(unsigned mm=0; mm<BigDimZ; mm++)
    {
        {
                if(     TemplateImageNew[2*nnc*BigDimZ+2*mm]      >
MaxValCorr )
            {
            MaxValCorr =  TemplateImageNew[2*nnc*BigDimZ+2*mm];
                MaxCorrIndex = mm;
            }
        }
    }
      return;
} void CrossCorrelation()
{

//include these two lines if no lateral correction is required
//    WallEdge1 = 55;
//    WallEdge2 = WallEdge1 + 530;
    MinDevIndexOld = (WallEdge1+WallEdge2)/2;
    WallOld1 = WallEdge1;
    WallOld2 = WallEdge2;
//remove these three lines if no lateral correction is required
     LateralCorrection(FirstSeg);
    if(LateralMax1 < RedoLateralCorrection)
       LateralCorrection(SecondSeg);
    AxialCorrection(SecondSeg);
    MakeHistogram(TemplateImage,SecondSeg);
       return;
} void MakeFileName(char *MFN1, unsigned MFN2, unsigned MFN3)
{
    if(MFN3==0)
       sprintf(MFN1,
"%spp%2.2d%2.2d%2.2d%2.2d\\PP%2.2d%2.2d%2.2d%2.2dindex.txt",
                                 DirectoryName,FileYear,
FileMonth,   FileDay,   FileSet,   FileYear,   FileMonth,   FileDay,
FileSet);
    if(MFN3==1)
```

```
    sprintf(MFN1,
"%spp%2.2d%2.2d%2.2d%2.2d\\PP%2.2d%2.2d%2.2d%2.2d%3.3dAVG.crw",
                            DirectoryName,FileYear,     FileMonth,
FileDay, FileSet, FileYear, FileMonth, FileDay, FileSet, MFN2);
    if(MFN3==2)
        sprintf(MFN1,
"%spp%2.2d%2.2d%2.2d%2.2d\\PP%2.2d%2.2d%2.2d%2.2d%3.3dAVG.raw",
DirectoryName,
                                        FileYear,      FileMonth,
FileDay, FileSet, FileYear, FileMonth, FileDay, FileSet, MFN2);
    return;
} void WriteCorrectedImage(float WCIdata[])
{
    int XCenter = (WallEdge1+WallEdge2)/2;
    if(XCenter >= ImageDimX/2)
    {
/*Quadrant 1*/
        if(CumulativeShift <= 0)
    {
            for(unsigned   jj=0;   jj<ImageDimX-XCenter+ImageDimX/2;
jj++)
            {
            for(int kk=ImageDimZ-1; kk>=-CumulativeShift; kk--)
    //      for(unsigned kk= -CumulativeShift; kk<ImageDimZ;
kk++)
                WCIdata[jj*ImageDimZ+kk]
                =                       WCIdata[(jj+XCenter-
ImageDimX/2)*ImageDimZ+kk+CumulativeShift];
            for(unsigned kk=0; kk<-CumulativeShift; kk++)
                WCIdata[jj*ImageDimZ+kk] = MaxVal;//0;
        }
            for(unsigned                         jj=(ImageDimX-
XCenter+ImageDimX/2)*ImageDimZ; jj<ImageDimX*ImageDimZ; jj++)
                WCIdata[jj] = MaxVal;//0;
        }
/*Quadrant 2*/
        if(CumulativeShift > 0)
        {
            for(unsigned          jj=0;           jj<ImageDimX-
XCenter+ImageDimX/2; jj++)
            {
            for(int kk=0; kk<ImageDimZ-CumulativeShift; kk++)
                WCIdata[jj*ImageDimZ+kk]
                =                       WCIdata[(jj+XCenter-
ImageDimX/2)*ImageDimZ+kk+CumulativeShift];
            for(unsigned         kk=ImageDimZ-CumulativeShift;
kk<ImageDimZ; kk++)
                WCIdata[jj*ImageDimZ+kk] = MaxVal;//0;
        }
```

```
            for(unsigned                              jj=(ImageDimX-
XCenter+ImageDimX/2)*ImageDimZ; jj<ImageDimX*ImageDimZ; jj++)
                WCIdata[jj] = MaxVal;//0;
        }
    }
    if(XCenter < ImageDimX/2)
    {
/*Quadrant 3*/
        if(CumulativeShift <= 0)
        {
            for(int    jj=ImageDimX-1;   jj>=(-XCenter+ImageDimX/2);
jj--)
            {
            for(int kk=ImageDimZ-1; kk>= -CumulativeShift; kk--)
        //    for(unsigned  kk= -CumulativeShift;  kk<ImageDimZ;
kk++)
                WCIdata[jj*ImageDimZ+kk]
                    =                          WCIdata[(jj+XCenter-
ImageDimX/2)*ImageDimZ+kk+CumulativeShift];
            for(unsigned kk=0; kk<-CumulativeShift; kk++)
                WCIdata[jj*ImageDimZ+kk] = MaxVal;//0;
            }
            for(unsigned  jj=0;  jj<(-XCenter+ImageDimX/2)*ImageDimZ;
jj++)
                WCIdata[jj] = MaxVal;//0;
        }
/*Quadrant 4*/
        if(CumulativeShift > 0)
        {
            for(int    jj=ImageDimX-1;   jj>=(-XCenter+ImageDimX/2);
jj--)
            {
            for(unsigned kk=0; kk<ImageDimZ-CumulativeShift; kk++)
        //    for(int kk=ImageDimZ-CumulativeShift-1; kk>=0; kk--
)
                WCIdata[jj*ImageDimZ+kk]
                    =                          WCIdata[(jj+XCenter-
ImageDimX/2)*ImageDimZ+kk+CumulativeShift];
            for(unsigned            kk=ImageDimZ-CumulativeShift;
kk<ImageDimZ; kk++)
                WCIdata[jj*ImageDimZ+kk] = MaxVal;//0;
            }
            for(unsigned  jj=0;  jj<(-XCenter+ImageDimX/2)*ImageDimZ;
jj++)
                WCIdata[jj] = MaxVal;//0;
        }
    }
    MakeFileName(ProcessedFilenameOut,CurrentPerspective,1);
    fstream ProcessedFile;
    ProcessedFile.open(ProcessedFilenameOut,ios::binary|ios::out);
    for(unsigned jj=0; jj<ImageDimZ; jj++)
    {
```

```cpp
        for(unsigned kk=0; kk<ImageDimX; kk++)
            ProcessedFile << WCIdata[kk*ImageDimZ+jj] << "\t";
    }
    ProcessedFile.close();
    return;
} void WriteToIndexFile()
{
    MakeFileName(IndexFilenameOut,0,0);
    fstream IndexFile;
    IndexFile.open(IndexFilenameOut,ios::binary|ios::app);
    IndexFile << WallEdge1 << "\t" << LateralMax1 << "\t" << MaxCorrIndex << "\t"
                                   << MaxValCorr << endl;
    IndexFile.close();
    return;
} void CalculateOffsets()
{
    MakeFileName(IndexFilenameOut,0,0);
    fstream IndexFile;
    IndexFile.open(IndexFilenameOut,ios::binary|ios::out);
    IndexFile.close();
       BigDims[0] = BigDimX;
    BigDims[1] = BigDimZ;
    MakeOneLine();
    for(CurrentPerspective=0;   CurrentPerspective<NumPerspectives;
CurrentPerspective++)
        {
        ReadUncorrectedImage(CurrentPerspective);
            CopyRawImage(ShiftedImage);
         CrossCorrelation();
         if(MaxCorrIndex>BigDimZ/2)
                CumulativeShift -= (BigDimZ-MaxCorrIndex);
         else
            CumulativeShift += MaxCorrIndex;
         WriteCorrectedImage(RawImage);
         WriteToIndexFile();
    }
        return;
} void ReadOffsets()
{
       double Junk;
    MakeFileName(IndexFilenameOut,0,0);
    fstream IndexFile;
    IndexFile.open(IndexFilenameOut,ios::binary|ios::in);
    for(unsigned jj=0; jj<2*NumPerspectives; jj++)
    {
```

```
        IndexFile >> (unsigned) CorrectedFile[jj];
        IndexFile >> Junk;
            cout << CorrectedFile[jj] << "\n";
    }
        IndexFile.close();
    for(CurrentPerspective=0;   CurrentPerspective<NumPerspectives;
CurrentPerspective++)
    {
        ReadUncorrectedImage(CurrentPerspective);
        WallEdge1 = CorrectedFile[2*CurrentPerspective];
        WallEdge2 = WallEdge1+530;
        MaxCorrIndex = CorrectedFile[2*CurrentPerspective+1];
        if(MaxCorrIndex>BigDimZ/2)
                CumulativeShift -= (BigDimZ-MaxCorrIndex);
        else
            CumulativeShift += MaxCorrIndex;
        cout << CumulativeShift << endl;
        WriteCorrectedImage(RawImage);
    }
        return;
} void main()
{
        int Calcoffs;
    GetFileInfo();
    printf("Calculate offsets? (Y/N)\n");
    Calcoffs = getch();
    if(Calcoffs == 'Y' || Calcoffs == 'y')
        CalculateOffsets();
    if(Calcoffs == 'N'|| Calcoffs == 'n')
        ReadOffsets();
    cout << "Done!" << endl;
    wait
}
```

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for correction of relative object-detector motion between successive views comprising the steps of:
    illuminating an object of interest to produce an image using a current view and a preceding view, wherein the current view and the preceding view are successive views, each successive view being taken from a different perspective;
    determining a lateral offset correction value for the image for each of the current view and the preceding view;
    determining an axial offset correction value for the image by finding a maximum in a cross-correlation function along a line that corresponds to a difference in the lateral offset correction values for the two views; and
    applying the lateral offset correction value and the axial offset correction value to the image to produce a corrected file image.

2. The method of claim 1, wherein the step of determining a lateral offset correction value for the image further comprises the steps of:
    thresholding the image; and
    cross-correlating the thresholded image with a template image.

3. The method of claim 2, wherein the template image is created by a method comprising the steps of:
    creating at least two white lines at predetermined positions to form a preliminary template image;
    expanding the preliminary template image to provide zero-padding in two dimensions resulting in an expanded template image; and
    performing a two-dimensional FFT on the expanded template image to create the final template image.

4. The method of claim 2, wherein the steps of thresholding the image and cross-correlating the image further comprise the steps of:
    finding the grayscale histogram of the image including a plurality of bins;
    identifying a bin with the greatest number of pixels;
    setting all pixels in the image having the identified bin's grayscale value or higher equal to zero in a copy of the image;
    applying a two-dimensional FFT to the copy of the image to produce a Fourier transform;
    multiplying the Fourier transform by a complex conjugate of the Fourier transform of the template image to produce a new image array;
    summing the new image array, along each of the plurality of rows to compute a lateral sum array;
    computing a one dimensional Fourier transform of the lateral sum array to find the cross-correlation of the rows of the copy of the original image and the template image;
    setting an uncorrected position of an image feature, at the location of the maximum value of the lateral sum array; and
    determining the lateral offset as the difference between the uncorrected position of the image feature and a predetermined position of the image feature.

5. The method of claim 4, further comprising the step of repeating the steps of thresholding the image and cross-correlating the image with a different number of bins in the histogram, if the maximum value of the cross-correlation has a magnitude less than a predetermined value.

6. The method of claim 4 wherein the image feature comprises a feature of a specimen container.

7. The method of claim 1, wherein the step of determining an axial offset correction value for the image further comprises the steps of:
    thresholding a copy of the current view of the image to produce a thresholded version of the image; and
    cross-correlating the thresholded version of the image with a thresholded version of a previous image before determining an axial offset.

8. The method of claim 1, wherein the step of determining an axial offset further comprises the steps of:
    finding the grayscale histogram of the current view of the image including a plurality of bins;
    identifying a peak bin with the greatest number of pixels;
    creating a thresholded image by setting all pixels in the current view of the image having the peak bin's grayscale value or higher equal to zero in a copy of the current view of the image;
    applying a low-pass filter to the thresholded image;
    computing a cross-correlation of the thresholded, low-pass filtered image with a preceding image's thresholded, low-pass filtered version;
    finding the maximum correction value in the row of the resultant cross-correlation that corresponds to the difference in the two images' lateral offsets; and
    adding the correction value to a sum of all previous axial offsets.

9. The method of claim 1 further comprising the steps of:
    writing the value of the lateral offset into an electronic memory device;
    writing the value of the axial offset into an electronic memory device; and
    generating a corrected image by cropping a plurality of pixels from one or two edges, as determined from the lateral and axial offsets, and shifting the remaining pixels by the number of the cropped plurality of pixels.

10. The method of claim 1, wherein the object of interest is a cell or a cell nucleus.

11. The method of claim 1 further comprising the steps of producing a plurality of images to generate an input image file; and cropping a plurality of the input image file images to produce a cropped copy of the input image file, with uncropped portions shifted vertically and/or horizontally, and with additional blank pixels inserted at one or two of the borders to retain the input image file size.

12. The method of claim 1 wherein the corrected file image comprises calculated offset values saved to a digital file.

13. The method of claim 12 wherein the calculated offset values are processed using computer word-processing to produce an altered text file, and the altered text file is used to generate offsets in two axes, and wherein the step for determining a lateral offset correction value for the image is iterated to find a maximum value.

14. The method of claim 12 wherein the calculated offset values comprise:
  a position of a maximum value of the cross-correlation between a current
  image and a template image;
  a maximum value of the cross-correlation between a current image and the template image;
  a location of a maximum correlation value on the corresponding row of a cross-correlation between the current image and the preceding image; and
  a maximum value of the cross-correlation between a current image and a preceding image.

15. A method for correction of relative object-detector motion between successive views comprising the steps of:
  imaging an object of interest to produce an image;
  determining a lateral offset correction value for the image;
  determining an axial offset correction value for the image, wherein the step of determining an axial offset correction value for the image is performed by thresholding the image, cross-correlating the image with the thresholded version of a previous image, and determining the axial offset correction value as a maximum in the cross-correlation function along a line that corresponds to a difference in lateral corrections of the two images; and
  applying the lateral offset correction value and the axial offset correction value to the image to produce a corrected file image.

* * * * *

UNITED STATES PATENT AND TRADEMARK OFFICE
CERTIFICATE OF CORRECTION

| | |
|---|---|
| PATENT NO. | : 7,260,253 B2 |
| APPLICATION NO. | : 10/876328 |
| DATED | : August 21, 2007 |
| INVENTOR(S) | : Rahn et al. |

It is certified that error appears in the above-identified patent and that said Letters Patent is hereby corrected as shown below:

Column 49,

Claim 14, Line 10, "the preceding image" should read --a preceding image--.

Signed and Sealed this

First Day of April, 2008

JON W. DUDAS
*Director of the United States Patent and Trademark Office*